(12) United States Patent
Stein et al.

(10) Patent No.: US 7,385,106 B2
(45) Date of Patent: Jun. 10, 2008

(54) PLANTS TOLERANT OF ENVIRONMENTAL STRESS CONDITIONS, METHODS OF GENERATING SAME AND NOVEL POLYNUCLEOTIDE SEQUENCE UTILIZED THEREBY

(75) Inventors: Hanan Stein, Nes Ziona (IL); Aviah Zilberstein, Holon (IL); Gadi Miller, Tel Aviv (IL); Yoram Kapulnik, Karmey Yosef (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 709 days.

(21) Appl. No.: 10/181,409

(22) PCT Filed: Jan. 10, 2001

(86) PCT No.: PCT/IL01/00026

§ 371 (c)(1),
(2), (4) Date: Oct. 30, 2002

(87) PCT Pub. No.: WO01/53323

PCT Pub. Date: Jul. 26, 2001

(65) Prior Publication Data

US 2003/0211490 A1  Nov. 13, 2003

(51) Int. Cl.
*A01H 5/00* (2006.01)
*C12N 15/82* (2006.01)

(52) U.S. Cl. .................... 800/298; 435/320.1; 435/419

(58) Field of Classification Search ............. 435/320.1; 800/289, 298, 285, 286
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,666,828 A | 5/1987 | Gusella | |
| 4,683,202 A | 7/1987 | Mullis | |
| 4,736,866 A | 4/1988 | Leder et al. | |
| 4,801,531 A | 1/1989 | Frossard | |
| 4,855,237 A | 8/1989 | Morinaga et al. | |
| 4,879,219 A | 11/1989 | Wands et al. | |
| 4,945,050 A | 7/1990 | Sanford et al. | |
| 5,011,771 A | 4/1991 | Bellet et al. | |
| 5,175,383 A | 12/1992 | Leder et al. | |
| 5,175,384 A | 12/1992 | Krimpenfort et al. | |
| 5,175,385 A | 12/1992 | Wagner et al. | |
| 5,192,659 A | 3/1993 | Simons | |
| 5,221,778 A | 6/1993 | Byrne et al. | |
| 5,272,057 A | 12/1993 | Smulson et al. | |
| 5,281,521 A | 1/1994 | Trojanowski et al. | |
| 5,288,846 A | 2/1994 | Quertermous et al. | |
| 5,298,422 A | 3/1994 | Schwartz et al. | |
| 5,316,931 A | 5/1994 | Donson et al. | |
| 5,344,923 A | 9/1994 | Verma et al. | |
| 5,347,075 A | 9/1994 | Sorge | |
| 5,360,735 A | 11/1994 | Weinshank et al. | |
| 5,387,742 A | 2/1995 | Cordell | |
| 5,451,513 A * | 9/1995 | Maliga et al. | ............... 800/278 |
| 5,464,764 A | 11/1995 | Capecchi et al. | |
| 5,487,992 A | 1/1996 | Capecchi et al. | |
| 5,639,950 A * | 6/1997 | Verma et al. | ............... 800/278 |
| 5,693,507 A | 12/1997 | Daniell et al. | |
| 5,717,084 A * | 2/1998 | Herrera-Estrella et al. | . 536/23.4 |

FOREIGN PATENT DOCUMENTS

| | | |
|---|---|---|
| EP | 067553 A2 | 12/1982 |
| EP | 0194809 A1 | 9/1986 |
| EP | 0278667 B1 | 8/1988 |
| WO | WO 87/06261 B1 | 8/1988 |
| WO | WO 93/14200 A1 | 7/1993 |
| WO | WO 94/06908 A1 | 3/1994 |
| WO | WO 94/23049 A3 | 10/1994 |
| WO | WO 94/28123 A1 | 12/1994 |

(Continued)

OTHER PUBLICATIONS

Kiyosue et al. A nuclear gene encoding mitochondrial proline dehydrogenase, an enzyme involved in proline metabolism, is upregulated by proline but downregulated by dehydration in *Arabidopsis*. Plant Cell. Aug. 1996;8(8):1323-35.*

(Continued)

*Primary Examiner*—Cynthia Collins

(57) ABSTRACT

A method of generating a plant tolerant of environmental stress conditions, the method comprising the step of expressing within the plant exogenous polynucleotides encoding enzymes capable of catalyzing proline production, wherein the exogenous polynucleotides are expressed in a manner so as to allow accumulation of the enzymes within a subcellular organelle of the plant. The invention further describes novel polynucleotides and nucleic acid constructs useful in implementing the methods and a transgenic plant resultant therefrom.

9 Claims, 13 Drawing Sheets

FOREIGN PATENT DOCUMENTS

WO      WO 99/66785      12/1999

OTHER PUBLICATIONS

Nakashima K. et al. A gene encoding proline dehydrogenase is not only induced by proline and hypoosmolarity, but is also developmentally regulated in the reproductive organs of *Arabidopsis*. Plant Physiol. Dec. 1998;118(4):1233-41.*

Hu C.A. et al. A bifunctional enzyme (delta 1-pyrroline-5-carboxylate synthetase) catalyzes the first two steps in proline biosynthesis in plants. Proc Natl Acad Sci U S A. Oct. 1, 1992;89(19):9354-8.*

Kishor P. et al. Overexpression of [delta]-Pyrroline-5-Carboxylate Synthetase Increases Proline Production and Confers Osmotolerance in Transgenic Plants. Plant Physiol. Aug. 1995;108(4):1387-1394.*

Nanjo T. et al. Antisense suppression of proline degradation improves tolerance to freezing and salinity in *Arabidopsis thaliana*. FEBS Lett. Nov. 19, 1999;461(3):205-10.*

Sokhansandzh A. et al. Transfer of bacterial genes for proline synthesis in plants and their expression by various plant promoters. English abstract from Genetika. Jul. 1997;33(7):906-13.*

Csonka L.N. et al. Nucleotide sequence of a mutation in the proB gene of *Escherichia coli* that confers proline overproduction and enhanced tolerance to osmotic stress. Gene. Apr. 29, 1988;64(2):199-205.*

Zhang C.S. et al. Removal of feedback inhibition of delta 1-pyrroline-5-carboxylate synthetase, a bifunctional enzyme catalyzing the first two steps of proline biosynthesis in plants. J Biol Chem. Sep. 1, 1995;270(35):20491-6.*

Szoke A. et al. Subcellular Location of Delta-Pyrroline-5-Carboxylate Reductase in Root/Nodule and Leaf of Soybean. Plant Physiol. Aug. 1992;99(4):1642-1649.*

Rayapati P.J. et al. Pyrroline-5-Carboxylate Reductase Is in Pea (*Pisum sativum* L.) Leaf Chloroplasts. Plant Physiol. Oct. 1989;91(2):581-586.*

Waterhouse et al. Virus resistance and gene silencing: killing the messenger. Trends Plant Sci. Nov. 1999;4(11):452-457.*

Puchta H. Gene replacement by homologous recombination in plants. Plant Mol Biol. Jan. 2002;48(1-2):173-82.*

Borsani O. et al. Endogenous siRNAs derived from a pair of natural cis-antisense transcripts regulate salt tolerance in *Arabidopsis*. Cell. Dec. 29, 2005;123(7):1279-91.*

Deleu C. et al. *Brassica napus* proline dehydrogenase (pdh) mRNA, partial cds, Genbank Accession No. AF171226, Aug. 11, 1999.*

Ballantyne JS, Chamberlin ME 1994 Regulation of cellular amino acid levels. In "Cellular and Molecular Physiology of Cell Volume Regulation" (K. Strange ed), CRC Press, Boca Raton, pp. 111-122.

Barnett NM, Naylor AW 1966 Amino acid and protein metabolism in Bermuda grass during water stress. Plant Physiol. 41: 1222-1230.

Bates LS, Waldren RP, Teare ID 1973 Rapid determination of free proline for water-stress studies. Plant and Soil 39:205-207.

Binzel ML, Hasegawa PM, Rhodes D, Handa S, Handa AK, Bressan RA 1987 Solute accumulation in tobacco cells adapted to NaCl. Plant Physiol. 84: 1408-1415.

Blum A, 1996 Crop responses to drought and the interpretation of adaptation. Plant Growth Regulation. 20: 135-148.

Blum A, Munns R, Passioura JB, Turner NC 1996 Genetically engineered plants resistant to soil drying and salt stress—how to interpret osmotic relations. Plant Physiol. 110:1051-1051.

Boggess SF, Aspinall D, Paleg LG 1976 Stress metabolism. IX. The significance of end-product inhibition of proline biosynthesis and of compartmentation in relation to stress-induced proline accumulation. Aust. J. Plant Physiol. 3: 513-52.

Brady CJ, Gibson TS, Barlow EWR, Spiers J, Wyn Jones RG 1984 Salt tolerance in plants. I. Ions, compatible solutes and the stability of plant ribosomes. Plant, Cell and Environ. 7: 571-578.

Briens M, Larher F 1982 Osmoregulation in halophytic higher plants: a comparative study of soluble carbohydrates, polyols, betaines and free proline. Plant, Cell & Environ. 5: 287-292.

Csonka LN 1981 Proline over-production results in enhanced osmotolerance in *Salmonella typhimurium*. Mol. Gen. Genet. 182: 82-86.

Csonka LN 1989 Physiological and genetic responses of bacteria to osmotic stress. Microbiol. Reviews 53: 121-147.

Csonka LN, Gelvin SB, Goodner BW, Orser CS, Siemieniak D, Slightom JL 1988 Nucleotide sequence of a mutation in the *proB* gene of *Escherichia coli* that confers proline overproduction and enhanced tolerance to osmotic stress, Gene 64: 199-205.

Delauney AJ, Verma DPS 1993 Proline biosynthesis and osmoregulation in plants. The Plant Journal 4: 215-223.

Dorffling K, Dorffling H, Lesselich G 1993 In vitro-selection and regeneration of hydroxyproline-resistant lines of winter wheat with increased proline content and increased frost tolerance. J. Plant Physiol. 142: 222-225.

Fujita T, Maggio A, Garcia-Rios M, Bressan RA, Csonka LN 1998 Comparative analysis of the regulation of expression and structures of two evolutionarily divergent genes for delta1-pyrroline-5-carboxylate synthetase from tomato. Plant Physiol. 118: 661-674.

Gibson TS, Spiers J, Brady CJ 1984 Salt tolerance in plants. II. In vitro translation of m-RNAs from salt-tolerant and salt-sensitive plants on wheat germ ribosomes: responses to ions and compatible solutes. Plant, Cell & Environ. 7: 579-587.

Ginzberg I, Stein H, Kapulnik Y, Szabados L, Strizhov N, Schell J, Koncz C, Zilberstein A 1998 Isolation and characterization of two different cDNAs of DELTA1-pyrroline-5-carboxylate synthase in alfalfa, transcriptionally induced upon salt stress. Plant Molecular Biology 38: 755-764.

Handa S, Handa AK, Hasegawa PM, Bressan RA 1986 Proline accumulation and the adaptation of cultured plant cells to water stress. Plant Physiol. 80: 938-945.

Hanson AD, Hitz WD 1982 Metabolic responses of mesophyts to plant water deficits. Annu. Rev. Plant Physiol. 33: 163-203.

Hare PD, Cress WA 1997 Metabolic implications of stress-induced proline accumulation in plants. Plant Growth Regulation 21: 79-102.

Hong-qi Z, Croes AF, Linskens HF 1982 Protein synthesis in germinating pollen of *Petunia*: role of proline. Planta 154: 199-203.

Hu CA, Delauney AJ, Verma DP 1992 A bifunctional enzyme (delta1-pyrroline-5-carboxylate synthetase) catalyzes the first two steps in proline biosynthesis in plants. Proc. Natl. Acad. Sci. USA 89: 9354-9358.

Jones MM, Osmund CB, Turner NC 1980 Accumulation of solutes in leaves of sorghum and sunflower in response to water deficits. Aust. J. Plant Physiol. 7: 193-205.

Katz A, Tal M 1980 Salt tolerance in the wild relatives of cultivated tomato: proline accumulation in callus tissue of *Lycopersicon esculentum* and *L. peruvianum*. Z. Pflanzenphysiol. Bd. 98: 429-435.

Ketchum REB, Warren RC, Klima LJ, Lopez-Gutierrez F, Nabors MW 1991 The mechanism and regulation of proline accumulation in suspension cultures of the halophytic grass *Distichlis spicata* L. J. Plant Physiol. 137: 368-374.

Kishor PBK, Hong Z, Miao G-H, Hu C-AA, Verma DPS 1995 Overexpression of delta-pyrroline-5-carboxylate synthetase increases proline production and confers osmotolerance in transgenic plants. Plant Physiol. 108: 1387-1394.

Kiyosue T, Yoshiba Y, Yamaguchi-Shinozaki K, Shinozaki K 1996 A nuclear gene, encoding mitochondrial proline dehydrogenase, an enzyme involved in proline metabolism, is upregulated by proline but downregulated by dehydration in *Arabidopsis*. The Plant Cell 8: 1323-1335.

Koncz C, Martini M, Mayerhofer R, Koncz-Kalman Z, Korber H, Redei GP, Schell J 1989 High-frequency T-DNA-mediated gene tagging in plants. Proc. Natl. Acad. Sci. USA 86:8467-8471.

Kueh JSH, Bright SWJ 1981 Proline accumulation in a barley mutant resistant to *trans*-4-hydroxy-L-proline. Planta 153: 166-171.

Lansac AR, Sullivan CY, Johnson BE 1996 Accumulation of free proline in sorghum (*Sorghum bicolor*) pollen. Can. J. Bot. 74: 40-45.

Leigh RA, Ahmad N, Wyn Jones RG 1981 Assessment of glycinebetaine and proline compartmentation by analysis of isolated beet vacuoles. Planta 153: 34-41.

Lone MI, Kueh JSH, Wyn Jones RG, Bright SWJ 1987 Influence of proline and glycinebetaine on slat tolerance of cultured barley embryos. J. Exp. Bot. 38: 479-490.

Low PS 1985 Molecular basis of the biological compatibility of nature's osmolytes. In "Transport Processes, Iono- and Osmoregulation" (R Gilles, M Gilles-Baillien eds), Springer-Verlag, Berlin, pp. 469-477.

Nash D, Paleg LG, Wiskich JT 1982 Effect of proline, betaine and some other solutes on the heat stability of mitochondrial enzymes. Aust. J. Plant Physiol. 9: 47-57.

Oaks A, Mitchell DJ, Barnard RA, Johnson FJ 1970 The regulation of proline biosynthesis in maize roots. Can. J. Bot. 48: 2249-2258.

Ober ES, RE 1994 Proline accumulation in maize (*Zea mays* L.) primary roots at low water potentials. I. Requirement for increased levels of abscisic acid. Plant Physiol. 105: 981-987.

Paleg LG, Douglas TJ, van Daal A, Keech DB 1981 Proline, betaine and other organic solutes protect enzymes against heat inactivation. Aust. J. Plant Physiol. 8: 107-114.

Paleg LG, Stewart GR, Bradbeer JW 1984 Proline and glycine betaine influence protein solvation. Plant Physiol. 75: 974-978.

Peng Z, Lu Q, Verma DP 1996 Reciprocal regulation of delta1-pyrroline-5-carboxylate synthetase and proline dehydrogenase genes control proline level during and after osmotic stress in plants. Mol. Gen. Genet. 253: 334-341.

Pollard A, Wyn Jones RG 1979 Enzyme activities in concentrated solutions of glycinebetaine and other solutes. Planta 144: 291-298.

Rhodes D 1987 Metabolic responses to stress. In "The Biochemistry of Plants" (DD Davies ed), vol. 12, Academic Press, New York, pp. 201-241.

Rhodes D, Handa S 1989 Amino acid metabolism in relation to osmotic adjustment in plant cells. In "Environmental Stress in Plants: Biochemical and Physiological Mechanisms", NATO ASI Series, vol. G19 (JH Cherry ed), Springer, Berlin, pp. 41-62.

Rhodes D, Handa S, Bressan RA 1986 Metabolic changes associated with adaptation of plant cells to water stress. Plant Physiol. 82: 890-903.

Roosens NHCJ, Thu TT, Iskander HM, Jacobs M 1998 Isolation of the ornithine-delta-aminotransferase cDNA and effect of salt stress on its expression in *Arabidopsis thaliana*. Plant Physiol. 117: 263-271.

Rudolph AS, Crowe JH, Crowe LM 1986 Effects of three stabilizing agents—proline, betaine and trehalose—on membrane phospholipids. Arch. Biochem. Biophys. 245: 134-143.

Samaras Y, Bressan RA, Csonka LN, Garcia-Rios MG, Paino D'Urzo M, Rhodes D 1995 Proline accumulation during drought and salinity. In (N Smirnoff ed) "Environment and Plant Metabolism: Flexibility and Acclimation," Bios Scientific Publishers, Oxford, pp. 161-187.

Santarius KA 1992 Freezing of isolated thylakoid membranes in complex media. VIII. Differential cryoprotection by sucrose, proline and glycerol. Physiol. Plant. 84: 87-93.

Santoro MM, Liu Y, Khan SMA, Hou L-X, Bolen DW 1992 Increased thermal stability of proteins in the presence of naturally occurring osmolytes. Biochemistry 31: 5278-5283.

Serrano R, Gaxiola R, 1994 Microbial Models and Salt Stress Tolerance in Plants. Critical Rev. in Plant Sci. 13: 121-138.

Sharp RE, Wu Y, Voetberg GS, Saab IN, LeNoble ME 1994 Confirmation that abscisic acid accumulation is required for maize primary root elongation at low water potentials. J. Exp. Bot. 45: 1743-1751.

Smirnoff N, Stewart GR, 1985 Stress metabolites and their role in coastal plants. Symposium on Coastal Vegetation. 62: 273-278.

Smirnoff N, Cumbes QJ 1989 Hydroxyl radical scavenging activity of compatible solutes. Phytochem. 28: 1057-1060.

Smith LT 1985 Characterization of a gamma-glutamyl kinase from *Escherichia coli* that confers proline overproduction and osmotic tolerance. J. Bacteriol. 164: 1088-1093.

Srinivas V, Balasubramanian D 1995 Proline is a protein-compatible hydrotrope. Langmuir 11: 2830-2833.

Stewart CR 1981 Proline accumulation: Biochemical aspects. In "Physiology and Biochemistry of Drought Resistance in Plants," (LG Paleg, D Aspinall eds) Academic Press, Sydney, pp. 243-259.

Stewart GR, Larher F 1980 Accumulation of amino acids and related compounds in relation to environmental stress. In "The Biochemistry of Plants" (BJ Miflin ed), vol. 5, Academic Press, New York, pp. 609-635.

Stewart GR, Lee JA 1974 The role of proline accumulation in halophytes. Planta 120: 279-289.

Strizhov N, Abraham E, Okresz L, Blickling S, Zilberstein A, Schell J, Koncz C, Szabados L 1997 Differential expression of two P5CS genes controlling proline accumulation during salt-stress requires ABA and is regulated by *ABA1*, *ABI1* and *AXR2* in *Arabidopsis*. Plant J. 12: 557-569.

Sumaryati S, Negrutiu I, Jacobs M 1992 Characterization and regeneration of salt- and water-stress mutants from protoplast culture of *Nicotiana plumbaginifolia* (Viviani). Theor. Appl. Genet. 83: 613-619.

Szoke A, Miao GH, Hong Z, Verma DPS 1992 Subcellular location of delta1-pyrroline-5-carboxylate reductase in root/nodule and leaf of soybean. Plant Physiol. 99: 1642-1649.

Tal M, Katz A 1980 Salt tolerance in the wild relatives of the cultivated tomato: the effect of proline on the growth of callus tissue of *Lycopersicon esculentum* and *L. peruvianum* under salt and water stress. Z. Pflanzenphysiol. Bd. 98: 283-288.

Taylor CB 1996 Proline and water deficit: ups and downs. The Plant Cell 8: 1221-1224.

Thomas JC, De Armond RL, Bohnert HJ 1992 Influence of NaCl on growth, proline, and phosphoenolpyruvate carboxylase levels in *Mesembryanthemum crystallinum* suspension cultures. Plant Physiol. 98: 626-631.

Thompson JF 1980 Arginine synthesis, proline synthesis, and related processes. In "The Biochemistry of Plants", vol. 5 (BJ Miflin ed) Academic Press, New York, pp. 375-403.

Treichel S 1975 The effect of NaCl on the concentration of proline in different halophytes. Z. Pflanzenphysiol. Bd. 76: 56-68.

Treichel S 1986 The influence of NaCl on delta$^1$-pyrroline-5-carboxylate reductase in proline-accumulating cell suspension cultures of *Mesembryanthemum nodiflorum* and other halophytes. Plant Physiol. 67: 173-181.

Voetberg GS, Sharp RE 1991 Growth of the maize primary root tip at low water potentials. III. Role of increased proline deposition in osmotic adjustment. Plant Physiol. 96: 1125-1130.

Yancey PH 1994 Compatible and counteracting solutes. In "Cellular and Molecular Physiology of Cell Volume Regulation" (K Strange ed), CRC Press, Boca Raton, pp. 81-109.

Yoshiba Y, Kiyosue T, Nakashima K, Yamaguchi-Shinozaki K, Shinozaki K 1997 Regulation of levels of proline as an osmolyte in plants under water stress. Plant Cell Physiol. 38: 1095-1102.

Zhang CS, Lu Q, Verma DP 1995 Removal of feedback inhibition of delta1-pyrroline-5-carboxylate synthetase, a bifunctional enzyme catalyzing the first two steps of proline biosynthesis in plants. J. Biol. Chem. 270: 20491-20496.

Goodwin, William, Jacqueline A. Pallas and Gareth I. Jenkins, Transcripts of a gene encoding a putative cell wall-plasma membrane linker protein are specifically cold-induced in *Brassica napus*, Plant Molecular Biology, 31: 771-781, 1996.

Deutch, Charles E., Ilga Winicov, Post-transcriptional regulation of a salt-inducible alfalfa gene encoding a putative chimeric proline-rich cell wall protein, Plant Molecular Biology, 27: 411-418, 1995.

Esaka Muneharu; Hiromi Hayakawa, Specific Secretion of Proline-Rich Proteins by Salt-Adapted Winged Bean Cells, Plant Cell Physiol, 36(3); 441-446 1995.

Bradley, J. Desmond, Per Kjellbom, Christopher J. Lamb, Elicitor- and Wound-Induced Oxidative Cross-Linking of a Proline-Rich Plant Cell Wall Protein: A Novel, Rapid Defense Response, Cell, vol. 70, 21-30, Jul. 10, 1992.

Nanjo et al. "Antisense Suppression of Proline Degradation Improves Tolerance to Freezing and Salinity in *Arabidopsis thaliana*", FEBS Letters, 461: 205-210, 1999. Claims: X: 3, 7-16. / Y: 1-30, 36, 37, 40.

Zhu et al., "Overexpression of a Delta1-Pyrroline-5-Carboxylate Synthetase Gene and Analysis of Tolerance to Water- and Salt-Stress in Transgenic Rice", Plant Science, 139(1): 41-48, 1998.

Kaye et al. "Characterization of a Gene for Spinach CAP160 and Expression of Two Spinach Cold-Acclimation Proteins in Tobacco", Plant Physiol, 116: 1367-1377, 1998.

* cited by examiner

```
   1 ..............................AGGTCAAGAAG   11
                                    ||||||||||
1401 CACAAGCATACACATTTTTGTATCTCATTACATTTTCATAGGTCAAGAAG 1450

12 AAAAAAAAATAATCAAAGGAAACTGGTTTTTTATTCATCATATCAAAACA   61
     ||||||||||||||||||||||||||||||||||||||||||||||||||
1451 AAAAAAAAATAATCAAAGGAAACTGGTTTTTTATTCATCATATCAAAACA 1500

62 TATATCTTCGTGTTTATATCATATAGATCATCTTTGACCGGTTGATGGCC  111
     ||||||||||||||||||||||||||||||||||||||||||||||||||
1501 TATATCTTCGTGTTTATATCATATAGATCATCTTTGACCGGTTGATGGCC 1550

112 ACCAGAGTAATCCCACCAAGAATTCTAAGGAAACTCCGATACAACACCGC  161
     ||||||||||||||||||||||||||||||||||||||||||||||||||
1551 ACCAGAGTAATCCCACCAAGAATTCTAAGGAAACTCCGATACAACACCGC 1600

162 CACAAAACCCTTCCAACCTGCCCTTACCTCGCCCGCTCTCGCTCCTACGT  211
     ||||||||||||||||||||||||||||||||||||||||||||||||||
1601 CACAAAACCCTTCCAACCTGCCCTTACCTCGCCCGCTCTCGCTCCTACGT 1650

212 CTAATATTTTAGACCAAAAACCGCCATCATCGACAACAACCCTCCTCCCT  261
     ||||||||||||||||||||||||||||||||||||||||||||||||||
1651 CTAATATTTTAGACCAAAAACCGCCATCATCGACAACAACCCTCCTCCCT 1700

262 CCCGACGCCGAGCTCAACTTCCACGACGTCGAAAAACTCTTTTCGCACGT  311
     ||||||||||||||||||||||||||||||||||||||||||||||||||
1701 CCCGACGCCGAGCTCAACTTCCACGACGTCGAAAAACTCTTTTCGCACGT 1750

312 CCCAACTACCAAACTTCTCAAATCAACTGCCATCCTCCATGCTACCGCGG  361
     ||||||||||||||||||||||||||||||||||||||||||||||||||
1751 CCCAACTACCAAACTTCTCAAATCAACTGCCATCCTCCATGCTACCGCGG 1800

362 TCGAGCCAATGGTTGACCTCGGTACATGGATGTTGAGGTCTGATCTCATG  411
     ||||||||||||||||||||||||||||||||||||||||||||||||||
1801 TCGAGCCAATGGTTGACCTCGGTACATGGATGTTGAGGTCTGATCTCATG 1850

412 CAGACCAATAATCCTTTACGTAACATTGCTATGGCTACCACACGTGCCAC  461
     ||||||||||||||||||||||||||||||||||||||||||||||||||
1851 CAGACCAATAATCCTTTACGTAACATTGCTATGGCTACCACACGTGCCAC 1900

462 TTTTTTCGATCATTTTTGTGCCGGAGAAGATGCTATCACCGCTGGAAAAA  511
     ||||||||||||||||||||||||||||||||||||||||||||||||||
1901 TTTTTTCGATCATTTTTGTGCCGGAGAAGATGCTATCACCGCTGGAAAAA 1950

512 GTATTGCCGGGTTGAATGAAGCCGGTTTACGTGGAATGCTGGTTTACGGC  561
     ||||||||||||||||||||||||||||||||||||||||||||||||||
1951 GTATTGCCGGGTTGAATGAAGCCGGTTTACGTGGAATGCTGGTTTACGGC 2000

562 GTTGAAGATGCTCATGATAACGCTGGCTGTGATCGCAATCTCAAAGGTTT  611
     ||||||||||||||||||||||||||||||||||||||||||||||||||
2001 GTTGAAGATGCTCATGATAACGCTGGCTGTGATCGCAATCTCAAAGGTTT 2050

612 TCTTCACACCGTTGATGTCAGCAGATCGCTTCCTCCATCTTC........  653
     ||||||||||||||||||||||||||||||||||||||||||
2051 TCTTCACACCGTTGATGTCAGCAGATCGCTTCCTCCATCTTCGGTAATCT 2100

654 ...........................................GGTAA   658
                                                 |||||
2651 TGTTATGTACTAATGTTTTCAAATTTAAACTTTTTTCTGTGTATAGGTAA 2700

659 GCTTTGTGATTGTGAAGATTACTGCAATATGTCCAATGAGTTTGCTTGAA  708
     ||||||||||||||||||||||||||||||||||||||||||||||||||
2701 GCTTTGTGATTGTGAAGATTACTGCAATATGTCCAATGAGTTTGCTTGAA 2750

709 AGAATGAGTGATTTGCTGAGATGGCAGAAGAAAGACCCTTCATTTGTTTT  758
     ||||||||||||||||||||||||||||||||||||||||||||||||||
2751 AGAATGAGTGATTTGCTGAGATGGCAGAAGAAAGACCCTTCATTTGTTTT 2800

759 ACCATGGAAGCAAGATTCATTGCCAATTTTCTCTGAGTCAAGTCCTTTGT  808
     ||||||||||||||||||||||||||||||||||||||||||||||||||
2801 ACCATGGAAGCAAGATTCATTGCCAATTTTCTCTGAGTCAAGTCCTTTGT 2850

809 ACCATACAAGGAAGAGACCAGAGCCATTAACAGCAGAAGAAGAGAGTGAT  858
     ||||||||||||||||||||||||||||||||||||||||||||||||||
2851 ACCATACAAGGAAGAGACCAGAGCCATTAACAGCAGAAGAAGAGAGTGAT 2900

859 CTTGATCTTGCTAACAAGAGATTCCTTGAGCTTTGTCAGAAATGTGTGCA  908
     ||||||||||||||||||||||||||||||||||||||||||||||||||
2901 CTTGATCTTGCTAACAAGAGATTCCTTGAGCTTTGTCAGAAATGTGTGCA 2950
```

Fig. 3

```
 909 AGCCAATATTCCATTATTGGTTGATGCTGAACATACTTCAGTTCAACCTG  958
     ||||||||||||||||||||||||||||||||||||||||||||||||||
2951 AGCCAATATTCCATTATTGGTTGATGCTGAACATACTTCAGTTCAACCTG 3000

959 CTATTGATTACTTTACTTACTCTTCTGCTATTATGCATAACAAAGGTGAA 1008
     |||||||||||||||||| |||||||||||||||||||||||||||||||
3001 CTATTGATTACTTTACTTACTCTTCTGCTATTATGCATAACAAAGGTGAA 3050

1009 AACCCTATTGTGTTTGGAACCCTTCAGACTTATTTGAAAGATGCTAAGGA 1058
     ||||||||||||||| ||||||||||||||||||||||||||||||||||
3051 AACCCTATTGTGTTTGAACCCTTCAGACTTATTTGAAAGATGCTAAGGA  3100

1059 GAGAATGTTGTTGGCATCAAAGGCTGCTGAGAAAATGGGGATACCAATGG 1108
     ||||||||||||||||||||||||||||||||||||||||||||||||||
3101 GAGAATGTTGTTGGCATCAAAGGCTGCTGAGAAAATGGGGATACCAATGG 3150

1109 GATTTAAGTTGGTTAGAGGTGCTTATATGTCTAGTGAAAGAAAATTGGCT 1158
     ||||||||||||||||||||||||||||||||||||| ||||||||||||
3151 GATTTAAGTTGGTTAGAGGTGCTTATATGTCTAGTGAAAGAAAATTGGCT 3200

1159 GCTGATTTGGGTTATGCTTCTCCAATTCATAACACTATTAAGGATACACA 1208
     ||||||||||||||||||||||||||||||||||||||||||||||||||
3201 GCTGATTTGGGTTATGCTTCTCCAATTCATAACACTATTAAGGATACACA 3250

1209 TAAGTGTTTCAATGATTGTTCAAATTACATGCTTGAGAAGATTGCTAATG 1258
     |||||||||||||||||||| |||||||||||||||||||||||||||||
3251 TAAGTGTTTCAATGATTGTTCAAATTACATGCTTGAGAAGATTGCTAATG 3300

1259 GTCCTGGTGGAGTTGTTCTTGCAACTCATAACATTGAATC.......... 1298
     ||||||||||||||||||||||||||||||||||||||||
3301 GTCCTGGTGGAGTTGTTCTTGCAACTCATAACATTGAATCAGGTATATAT 3350

1299 ...............................AGGAAAATTGGCTGCTGCAA 1318
                                     ||||||||||||||||||
3401 TGAGTTTGATTTAATTAATGATTTTTGTATAGGAAAATTGGCTGCTGCAA 3450

1319 AAGCACATGAATTAGGGATTGGAAAGGTGAACCATAAGATGGAATTTGCA 1368
     ||||||||||||||||||||||||||||||||||||||||||||||||||
3451 AAGCACATGAATTAGGGATTGGAAAGGTGAACCATAAGATGGAATTTGCA 3500

1369 CAACTATATGGAATGTCTGAGGCACTATCTTTTGGTTTAAGCAATGCAGG 1418
     ||||||||||||||||||||||||||||||||||||||||||||||||||
3501 CAACTATATGGAATGTCTGAGGCACTATCTTTTGGTTTAAGCAATGCAGG 3550

1419 GTTTCAAGTTAGCAAGTATATGCCATTTGGTCCTGTGGAGACTGTTATGC 1468
     ||||||||||||||||||||||||||||||||||||||||||||||||||
3551 GTTTCAAGTTAGCAAGTATATGCCATTTGGTCCTGTGGAGACTGTTATGC 3600

1469 CATACCTCTTGAGAAGGGCTGAGGAGAATAGAGGAGTGTTGGCTGCATCA 1518
     ||||||||||||||||||||||||||||||||||||||||||||||||||
3601 CATACCTCTTGAGAAGGGCTGAGGAGAATAGAGGAGTGTTGGCTGCATCA 3650

1519 GGCTTTGACAGGCAACTGATG............................ 1539
     |||||||||||||||||||||
3651 GGCTTTGACAGGCAACTGATGAGGTAAAAATTTCAAAAAAATTTACCATT 3700

1540 ..........AGGAAGGAGTTGGTCAGGAGAGTAAAAGCTTCTGTGCTT  1578
               ||||||||||||||||||||||||||||||||||||||||
3751 TTTTGTGTAACAGGAAGGAGTTGGTCAGGAGAGTAAAAGCTTCTGTGCTT 3800

1579 TAAATTTGTTGGATGAGTTGATGGGATGTAATAATGTAGGCAACAGGGTT 1628
     ||||||||||||||||||||||||||||||||||||||||||||||||||
3801 TAAATTTGTTGGATGAGTTGATGGGATGTAATAATGTAGGCAACAGGGTT 3850

1629 CACCATTCTGTGTACAAATTAGAGAGAATCCTGTAATTTGCTTAAATTTT 1678
     ||||||||||||||||||||||||||||||||||||||||||||||||||
3851 CACCATTCTGTGTACAAATTAGAGAGAATCCTGTAATTTGCTTAAATTTT 3900

1679 GTGCATTCAAGTTAATGAAATGTGCATTTGTCTTAAGTGTATTGATCCAC 1728
     ||||||||||||||||||||||||||||||||||||||||||||||||||
3901 GTGCATTCAAGTTAATGAAATGTGCATTTGTCTTAAGTGTATTGATCCAC 3950

1729 ATTTCCACTTGTTTGTACATTAATGCCATTGAATTGTTTAAGAAATTGTT 1778
     ||||||||||||||||||||||||||||||||||||||||||||||||||
3951 ATTTCCACTTGTTTGTACATTAATGCCATTGAATTGTTTAAGAAATTGTT 4000

1779 ATTCATAAAGTGTCTTATGTGTTTGAGGTGATTCCAAAAAAAAAAAAAAA 1828
     ||||||||||||||||||||||||||||||||||||||
4001 ATTCATAAAGTGTCTTATGTGTTTGAGGTGATTCC............... 4035
```

Fig. 3(cont.)

PLANTS TOLERANT OF ENVIRONMENTAL STRESS CONDITIONS, METHODS OF GENERATING SAME AND NOVEL POLYNUCLEOTIDE SEQUENCE UTILIZED THEREBY

RELATED PATENT APPLICATIONS

This application is a National Phase Application of PCT/IL01/00026 filed 10 Jan. 2001, which claims priority from U.S. application Ser. No. 09/490,454 filed 24 Jan. 2000, which is still pending.

FIELD AND BACKGROUND OF THE INVENTION

The present invention relates to methods of generating plants tolerant of extreme environmental stress conditions and to plants generated thereby. More particularly, the methods of the present invention are effected by over expression of enzymes involved in the biosynthesis of proline and/or downregulation of endogenous proline degrading enzymes. The present invention also relates to polynucleotides including a novel stress sensitive promoter and encoding a novel proline dehydrogenase (oxidase) enzyme which catalyses the first step in plant proline degradation and as such, can be specifically targeted for downregulation in order to increase proline level in plants.

Environmental conditions such as high salinity, drought and extreme temperatures severely limit plant growth and/or yield and as such, geographical locations which are characterized by such environmental conditions are typically devoid of crop plants.

Extreme environmental conditions typically lead to a lack of available water molecules which in turn leads to osmotic stress in the plant. Water loss from a plant grown under such conditions can be counteracted for a short period of time via various stress tolerance mechanisms, which are sometimes species-specific.

Stress tolerance is a multi-gene trait, encompassing various biochemical metabolic pathways which are found in bacteria, fungi, algae and plants.

The best characterized biochemical response of plant cells to osmotic stress is the synthesis of special organic solutes (osmolytes) which accumulate at high cytoplasmic concentrations and as such elevate the internal osmotic pressure to eliminate water loss from the cell and restore cell volume and turgor (Serrano and Gaxiola, 1994).

Under low water conditions, when the water potential of the soil in the rooting zone declines and shoot transpiration is limited, plants generate a gradient of negative water potential throughout the root and shoot tissues up to the leaves such that water from the soil can be driven to the upper parts of the shoots.

To generate such a gradient, plants have developed osmotic adjustment ability in which gradual accumulation of solutes is effected by the cells in order to decrease their water potential without any accompanying decrease in turgor. The accumulation of ions during osmotic adjustment appears to occur mainly within the vacuoles, where the ions are kept out of contact with enzymes in the cytosol or sub-cellular organelles. Because of this compartmentation of ions, other solutes must accumulate in the cytoplasm to maintain water potential equilibrium within the cell. These solutes, which are termed compatible solutes or osmolytes, are organic compounds that do not interfere with intracellular enzyme functions (Taiz and Zeiger, 1991).

Plant osmolytes are typically uncharged at neutral pH, and highly soluble in water (Ballantyne and Chamberlin, 1994). In addition, at high concentrations osmolytes have little or no perturbing effect on macromolecule-solvent interactions (Yancey, 1994). Furthermore, unlike perturbing solutes (such as inorganic ions) which readily enter the hydration sphere of proteins, thus favoring unfolding, compatible osmolytes tend to be excluded from the hydration sphere of proteins and as such stabilize folded protein structures (Low, 1985).

Proline is the most common osmolyte and is accumulated by a variety of organisms including bacteria, fungi, algae, invertebrates and plants (for review see Delauney and Verma, 1993, Hare and Cress, 1997). Other well-studied osmolytes include sugar alcohols like sorbitol and quaternary amines, such as glycine-betaine.

Solutes accumulation under stress (osmotic adjustment) is probably the most distinctive feature of an adaptive response to stresses linked to water deficit, such as drought, freezing and salinity.

Osmotic adjustment takes time, while fast reduction in plant water status during imposition of osmotic shock does not leave enough time for adjustment. This implies that osmotic adjustment may not be a very effective mechanism for conferring drought resistance when plants are grown in very light tropical or sandy soils, which are characterized by a very low water holding capacity (Blum, 1996). Therefore, acquiring high levels of cellular osmolytes in genetically modified plants could improve their osmotic tolerance when grown in such rapidly changing environments.

Proline and Stresses:

In higher plants, proline accumulation is a common metabolic response to water deficit and salinity stress, and as such, proline accumulation has been the subject of numerous reviews over the last 20 years (see for example, Stewart and Larher, 1980; Thompson, 1980; Stewart, 1981; Hanson and Hitz, 1982; Rhodes, 1987; Delauney and Verma, 1993; Samaras et al., 1995; Taylor, 1996).

Proline also appears to be the preferred organic osmolyte in many other organisms. Genetic studies in prokaryotes demonstrated that proline is an essential compatible solute capable of conferring osmo-protection (Csonka, 1989). Increased osmo-tolerance of bacteria has been achieved by proline over-production caused by altered feedback inhibition of the proline biosynthesis pathway (Csonka, 1981; Smith, 1985).

Numerous studies have linked proline accumulation in plants to high salinity conditions, water deprivation, high and low temperature, toxicity of heavy metals, pathogen infections, anaerobiosis, nutrient deficiencies, atmospheric pollution and UV irradiation.

For example, soluble proline accumulates in leaves of many halophytic higher plant species grown in saline environments (Stewart and Lee, 1974; Treichel, 1975; Briens and Larher, 1982), in leaf tissues and shoot apical meristems of plants grown under water stress (Barnett and Naylor, 1966; Boggess et al., 1976; Jones et al., 1980), in desiccating pollen (Hong-qi et al., 1982; Lansac et al., 1996), in root apical regions grown under a low water potential (Voetberg and Sharp, 1991), and in suspension cultures of plant cells adapted to water stress (Tal and Katz, 1980; Handa et al., 1986; Rhodes et al., 1986), or NaCl stress (Katz and Tal, 1980; Tal and Katz, 1980; Treichel, 1986; Binzel et al., 1987; Rhodes and Handa, 1989; Thomas et al., 1992).

Studies reviewed by Hare and Cress (1997) pointed out that during the imposition of a stress, an increase in proline level in planta is linked to the amelioration of negative physiological effects. Analysis of experimental evidence collected from many studies suggests that proline accumulation may also serve to protect membranes and proteins against the adverse effects of high concentrations of inorganic ions and temperature extremes (Pollard and Wyn Jones, 1979; Paleg et al., 1981; Nash et al., 1982; Paleg et al., 1984; Brady et al., 1984; Gibson et al., 1984; Smirnoff and Stewart, 1985; Rudolph et al., 1986; Santarius, 1992; Santoro et al., 1992), as a protein-compatible hydrotope (Srinivas and Balasubramanian, 1995), and as a hydroxyl radical scavenger (Smirnoff and Cumbes, 1989).

Under conditions of water or salinity stress in plants, proline accumulates primarily in the cell cytosol (Leigh et al., 1981; Ketchum et al., 1991). For example, in cell cultures of tobacco which were adapted for growth under 428 mM NaCl proline represents over 80% of the free amino acid pool (Rhodes and Handa, 1989). Thus, assuming a uniform distribution of proline in the cytosol, this amino acid is present in the cell cytosol at a concentration of 129 mM (Binzel et al, 1987). However, if confined to the cytoplasm, the concentration of proline could exceed 200 mM in these cells and therefore contribute substantially to cytoplasmic osmotic adjustment (Binzel et al., 1987). Similarly, the cytosolic proline concentration of salt stressed *Distichlis spicata* cells (treated with 200 mM NaCl) is estimated at around 230 mM (Ketchum et al. 1991).

Proline represents a major solute in the apical millimeter of maize roots, reaching concentrations of 120 mM in roots growing at water potential of −1.6 MPa (Voetberg and Sharp, 1991). The accumulated proline accounts for a significant fraction (about 50%) of the osmotic adjustment in this region (Voetberg and Sharp, 1991). In response to a water deficit, proline accumulates in maize root apical meristems with a marked increase of proline deposition in the growing region; this accumulation appears to be abscisic acid (ABA) dependent (Ober and Sharp, 1994; Sharp et al., 1994). Although maize roots are known to synthesize proline (Oaks et al., 1970), at present it is unclear whether increased deposition of proline in the apical region is a consequence of increased transport to the apex via the phloem, or local de novo synthesis of proline in the apex (Voetberg and Sharp, 1991).

Studies conducted on hydroxyproline-resistant mutants of barley and winter wheat have identified plant lines that accumulate greater quantities of proline than wild-type (Kueh and Bright, 1981; Dorffling et al., 1993). In winter wheat the hydroxyproline-resistant lines are significantly more frost tolerant than wild-type (Dorffling et al., 1993). However, it appears that the concentrations of proline accumulated in these mutants may be an order of magnitude lower than that required to produce a significant physiological effect on osmotic stress tolerance (Lone et al., 1987).

Under stress conditions, proline synthesis is also participates in alleviating cytoplasmic acidosis, and may maintain NADP+/NADPH ratios at values compatible with metabolism (Hare and Cress, 1997). Rapid catabolism of proline upon relief of stress may provide reducing equivalents that support mitochondrial oxidative phosphorylation and the generation of ATP useful for recovery from stress and repair of stress-induced cellular damage (Hare and Cress, 1997).

Proline Biosynthiesis:

In *E. coli*, the first two steps in the proline synthesis pathway (FIG. 1) are catalyzed by an enzymatic complex formed from gamma-glutamyl kinase (GK), which is encoded by the proB gene, and gamma-glutamylphosphate reductase (GPR or GSD), which is encoded by proA. The delta-pyrroline-5-carboxylate (P5C) product generated by the complex, or from the arginine biosynthesis pathway (FIG. 1), is immediately reduced to proline in a reaction catalyzed by delta-pyrroline-5-carboxylate reductase (P5CR), which is encoded by proC.

The first enzyme, GK, is feedback regulated by proline and, therefore, proline accumulation does not occur in wild-type *E. coli* cells. The *E. coli* proB74 mutated gene encodes a modified GK enzyme, which is insensitive to high proline concentrations of up to 100 mM, and which, therefore, can drive proline synthesis in the presence of high proline concentration in the cells. The proB74 gene differs at position 107 of the ProB (GK) amino acid sequence (aspartic acid to asparagin). Increased proline production and osmo-tolerance in bacteria has been observed in mutants carrying the proB74 gene (Csonka et al., 1988).

In young plants, proline is produced from either glutamate or ornithine (FIG. 1), while in mature plants or during the exposure to stress the glutamate pathway usually dominates (Roosens et al., 1998). A bifunctional enzyme, delta-pyrroline-5-carboxylate synthase (P5CS, FIG. 1) catalyzes the first two steps of P5C formation and shows a certain homology to the deduced amino acid sequence of the bacterial proB and proA Fujita et al., 1998; Ginzberg et al., 1998; Hu et al., 1992; Strizhov et al., 1997). It is assumed that P5CS activity is confined to the cytosol, since full length P5CS cDNAs isolated thus far lack a defined plastid-targeting transit-peptide sequence.

The activity of P5CS is feedback regulated by concentrations of proline as low as 10 mM (Hu et al., 1992). Expression of a cDNA encoding a wild-type P5CS of Vigna in tobacco rendered the recipient plants relatively tolerant to salt stress (Kishor et al., 1995), despite the enzyme's sensitivity to low proline concentrations. However, the measurements relating to osmotic adjustment which were performed in these transgenic plants, were not accepted by some plant physiologists (Blum et al., 1996).

U.S. Pat. No. 5,639,950 to Verma et al., describes the production of plants containing a cDNA clone encoding P5CS, with both gamma-glutamyl kinase and glutamic-gamma-semialdehyde dehydrogenase activities that catalyzes the first two steps in plant proline biosynthesis. This invention also provides methods for increasing the salt tolerance and drought resistance of plants, and for increasing the proline production activity in plants.

A mutated P5CS, showing relative insensitivity to proline inhibition was generated via site directed mutagenesis (Zhang et al., 1995). Such a mutant may further increase proline accumulation when expressed in transgenic plants. However, the presence of P5CS inhibitor that inactivates its enzymatic activity in roots (Zhang et al., 1995) may negatively affect activity of both endogenous as well as exogenous P5CSs at the primary site exposed to salinity stress.

Studies in which overexpression of P5CR (FIG. 1) was effected in transgenic plants, did not alter the proline level therein, and as such this enzyme is not considered a likely candidate for overexpression in plants (Szoke et al., 1992).

Proline Degradation in Plants:

Proline oxidation to glutamate is carried out in the mitochondria by the sequential action of proline dehydrogenase (PDh) and P5C-dehydrogenase (P5C-Dh) (FIG. 1). Both enzymes are bound to the matrix side of the inner mitochondrial membrane. A cDNA encoding PDh has been isolated from *Arabidopsis* (Kiyosue et al., 1996). Two forms of the second enzyme P5C-Dh have also been identified in plants but their corresponding genes have not been isolated (Forlani et al., 1997).

Transcription and Activity of Proline Biosynthesis and Begradation Enzymes During Stress Imposition and Relief:

Analysis of transcription during stress and recovery periods showed that the levels of P5CS transcripts were elevated during stress and gradually diminished during the post-stress period (Ginzberg et al., 1998; Peng et al., 1996; Strizhov et al., 1997; Yoshiba et al., 1997).

Conversely, transcript levels of PDh gradually reduced within several hours of stress, and rapidly increased upon relief from stress (Peng et al., 1996; Yoshiba et al., 1997). PDh transcript levels also increased by exogenously applied proline (Peng et al., 1996). The enzymatic activities in vitro of PDh and P5C-Dh have been reported to be strongly reduced by high concentrations of Cl⁻ anions, while in intact cells no conspicuous Cl⁻ inhibition of P5C-Dh form I has been recorded (Forlani et al., 1997; Peng et al., 1996).

Although the prior art documents mentioned hereinabove describe methods for increasing the proline level in plants, the increase in proline level demonstrated by these methods falls short of that observed in wild type plants grown under extreme environmental stress conditions which is approximately 40-300 times higher than that of non-stressed plants. As such, it is believed that these prior art methods cannot effectively produce a desired osmotic protective effect under conditions of extreme stress.

Thus, the present invention relates to a method for generating a plant tolerant of environmental stress conditions, which plant is capable of accumulating high levels of proline. Generating plants tolerant of environmental stress conditions according to the present invention is effected by increasing proline biosynthesis in the plant via overexpression of exogenous prokaryotic or eukaryotic proline biosynthetic enzymes, preferably in the chloroplast, and in addition or alternatively blocking or downregulating the activity of endogenous enzymes, such as proline dehydrogenase (PDh) and P5C-Dh, which are responsible for proline degradation. The present invention further relates to an alfalfa (*Medicago sativa*) gene including a novel stress sensitive promoter and further encoding a novel proline dehydrogenase (oxidase) enzyme which catalyses the first step in plant proline degradation and as such can be specifically targeted for downregulation.

SUMMARY OF THE INVENTION

According to one aspect of the present invention there is provided an isolated nucleic acid comprising a genomic, complementary or composite polynucleotide sequence encoding a polypeptide at least 65% homologous to SEQ ID NO:5 as determined using the BestFit software of the Wisconsin sequence analysis package, utilizing the Smith and Waterman algorithm, where gap creation penalty equals 8 and gap extension penalty equals 2.

According to another aspect of the present invention there is provided an isolated nucleic acid comprising a genomic, complementary or composite polynucleotide sequence hybridizable with SEQ ID NOs:4 or 6 under hybridization conditions of hybridization solution containing 10% dextrane sulfate, 1 M NaCl, 1% SDS and 5×10⁶ cpm ³²p labeled probe, at 65° C., with a final wash solution of 2×SSC and 0.1% SDS and final wash at 50° C.

According to yet another aspect of the present invention there is provided an isolated nucleic acid comprising a genomic, complementary or composite polynucleotide sequence at least 60% identical with SEQ ID NOs:4 or 6 as determined using the BestFit software of the Wisconsin sequence analysis package, utilizing the Smith and Waterman algorithm, where gap weight equals 50, length weight equals 3, average match equals 10 and average mismatch equals −9.

According to firer features in preferred embodiments of the invention described below, the polynucleotide sequence encodes a polypeptide functional as a proline dehydrogenase and having a sequence as set forth in SEQ ID NO:5.

According to still further features in the described preferred embodiments polynucleotide sequence as set forth in SEQ ID NOs:4 or 6.

According to still another aspect of the present invention there is provided a nucleic acid construct comprising at least a portion of any of the isolated nucleic acids described herein and optionally a promoter, wherein the isolated nucleic acid is in sense or antisense orientation with respect to the promoter, which regulates its expression.

According to an additional aspect of the present invention there is provided a transformed plant, plant derived tissue or plant cell comprising any of the isolated nucleic acids and/or the nucleic acid constructs described herein.

According to yet an additional aspect of the present invention there is provided an oligonucleotide of at least 17 bases specifically hybridizable with the isolated nucleic acids described herein.

According to still an additional aspect of the present invention there is provided a pair of oligonucleotides each of at least 17 bases specifically hybridizable with the isolated nucleic acid of claim 1 in an opposite orientation so as to direct exponential amplification of a portion thereof in a nucleic acid amplification reaction.

According to a further aspect of the present invention there is provided a nucleic acid amplification product obtained using the pair of primers described herein.

According to yet a further aspect of the present invention there is provided an antisense oligonucleotide comprising a polynucleotide of at least 10 bases being specifically hybridizable with a portion of a polynucleotide strand encoding a polypeptide at least 65% homologous to SEQ ID NO:5 as determined using the BestFit software of the Wisconsin sequence analysis package, utilizing the Smith and Waterman algorithm, where gap creation penalty equals 8 and gap extension penalty equals 2.

According to still a further aspect of the present invention there is provided an antisense oligonucleotide comprising a polynucleotide of at least 10 bases being specifically hybridizable with a portion of a polynucleotide at least 60% identical with SEQ ID NOs:4 or 6 as determined using the BestFit software of the Wisconsin sequence analysis package, utilizing the Smith and Waterman algorithm, where gap weight equals 50, length weight equals 3, average match equals 10 and average mismatch equals −9.

According to one aspect of the present invention there is provided an antisense oligonucleotide comprising a polynucleotide of at least 10 bases being specifically hybridizable with a portion of a polynucleotide hybridizable with SEQ ID NOs:4 or 6 under hybridization conditions of hybridization solution containing 10% dextrane sulfate, 1 M NaCl, 1% SDS and 5×10⁶ cpm ³²p labeled probe, at 65° C., with a final wash solution of 2×SSC and 0.1% SDS and final wash at 50° C.

According to another aspect of the present invention there is provided a ribozyme comprising any of the antisense oligonucleotides described herein and a ribozyme sequence.

According to yet another aspect of the present invention there is provided a recombinant protein comprising a polypeptide at least 65% homologous to SEQ ID NO:5 as determined using the BestFit software of the Wisconsin sequence analysis package, utilizing the Smith and Waterman algorithm, where gap creation penalty equals 8 and gap extension penalty equals 2.

According to further features in preferred embodiments of the invention described below, the recombinant protein having a proline dehydrogenase activity.

According to still further features in the described preferred embodiments the polypeptide is encoded by a polynucleotide hybridizable with SEQ ID NOs:4 or 6 or a portion thereof under hybridization conditions of hybridization solution containing 10% dextrane sulfate, 1 M NaCl, 1% SDS and $5\times10^6$ cpm $^{32}$p labeled probe, at 65° C., with a final wash solution of 1×SSC and 0.1% SDS and final wash at 50° C.

According to still further features in the described preferred embodiments the polypeptide is encoded by a polynucleotide at least 60% identical with SEQ ID NOs:4 or 6 or portions thereof as determined using the BestFit software of the Wisconsin sequence analysis package, utilizing the Smith and Waterman algorithm, where gap weight equals 50, length weight equals 3, average match equals 10 and average mismatch equals −9.

According to still further features in the described preferred embodiments the polypeptide is as set forth in SEQ ID NO:5.

According to still another aspect of the present invention there is provided an isolated nucleic acid comprising a polynucleotide being hybridizable with SEQ ID NOs:7 or 8 under hybridization conditions of hybridization solution containing 10% dextrane sulfate, 1 M NaCl, 1% SDS and $5\times10^6$ cpm $^{32}$p labeled probe, at 65° C., with a final wash solution of 2×SSC and 0.1% SDS and final wash at 50° C.

According to an additional aspect of the present invention there is provided an isolated nucleic acid comprising a polynucleotide at least 60% identical with SEQ ID NOs:7 or 8 as determined using the BestFit software of the Wisconsin sequence analysis package, utilizing the Smith and Waterman algorithm, where gap weight equals 50, length weight equals 3, average match equals 10 and average mismatch equals −9.

According to further features in preferred embodiments of the invention described below, the isolated nucleic acid having a plant promoter activity and is preferably as set forth in SEQ ID NOs:7 or 8.

According to yet an additional aspect of the present invention there is provided a nucleic acid construct comprising the isolated nucleic acid functional as a promoter.

According to still an additional aspect of the present invention there is provided a transformed plant, plant derived tissue or plant cell comprising the nucleic acid functional as a promoter.

According to a further aspect of the present invention there is provided an oligonucleotide of at least 17 bases specifically hybridizable with the isolated nucleic acid functional as a promoter.

According to yet a further aspect of the present invention there is provided a nucleic acid construct comprising (a) a first polynucleotide region encoding a first enzyme participating in the biosynthesis of proline and a first leader peptide being in frame thereto for targeting the first enzyme into a subcellular organelle of a plant cell.

According to further features in preferred embodiments of the invention described below, a nucleic acid construct comprising an isolated nucleic acid comprising a polynucleotide being hybridizable with SEQ ID NOs:7 or 8 under hybridization conditions of hybridization solution containing 10% dextrane sulfate. 1 M NaCl, 1% SDS and $5\times10^6$ cpm$^{32}$P labeled probe. at 65° C., with a final wash solution of 2x SSC and 0.1% SDS and final wash at 50 ° C., further comprising (b) a second polynucleotide region encoding a second enzyme participating in the biosynthesis of proline and a second leader sequence for targeting the second enzyme into the subcellular organelle of the plant cell.

According to still further features in the described preferred embodiments the first enzyme is a bacterial enzyme.

According to still further features in the described preferred embodiments the first enzyme is a plant enzyme.

According to still further features in the described preferred embodiments the first enzyme is selected from the group consisting of gamma-glutamyl kinase (GK) and gamma-glutamylphosphate reductase (GPR or GSD).

According to still further features in the described preferred embodiments a nucleic acid construct comnrising an isolated nucleic acid comprising a polynucleotide being hybridizable with SEQ ID NOs:7 or 8 under hybridization conditions of hybridization solution containing 10% dextrane sulfate. 1 M NaCl, 1% SDS and $5 \times 10^6$ cpm $^{32}$P labeled probe, at 65° C.. with a final wash solution of 2×SSC and 0.1% SDS and final wash at 50 ° C., further comprising (b) a second polynucleotide region encoding a polynucleotide capable of hybridizing under physiological conditions to an endogenous gene expressed in the plant cell, the endogenous gene encoding a second enzyme participating in the degradation of proline.

According to still further features in the described preferred embodiments the second enzyme is selected from the group consisting of proline dehydrogenase (PDh) and P5C-dehydrogenase (P5C-Dh).

According to still further features in the described preferred embodiments the subcellular organelle is a chloroplast.

According to still a further aspect of the present invention there is provided a plant, plant derived tissue or a plant cell comprising any of the expression constructs described hereinabove.

According to another aspect of the present invention there is provided a transgenic plant comprising a level of proline at least twenty fold higher than that of a non-transgenic isogenic plant, wherein both plants are grown under optimal conditions which result in lowest proline content is the non-transgenic isogenic plant.

According to yet another aspect of the present invention there is provided a plant seedling comprising a level of proline at least fifty folds higher than that of a non-transgenic isogenic plant seedling, wherein both plant seedlings are grown under optimal conditions which result in lowest proline content is the non-transgenic isogenic plant seedling.

According to still another aspect of the present invention there is provided a plant tolerant of environmental stress conditions, the plant comprising exogenous polynucleotides encoding enzymes capable of catalyzing proline production, wherein the exogenous polynucleotides are expressed in the plant in a manner so as to allow accumulation of the enzymes within a subcellular organelle of the plant.

According to an additional aspect of the present invention there is provided a method of generating a plant tolerant of environmental stress conditions, the method comprising the step of expressing within the plant exogenous polynucleotides encoding enzymes capable of catalyzing proline production, wherein the exogenous polynucleotides are expressed in a manner so as to allow accumulation of the enzymes within a subcellular organelle of the plant.

According to further features in preferred embodiments of the invention described below, the enzymes are expressed in the subcellular organelle of the plant.

According to still further features in the described preferred embodiments the enzymes are targeted into the subcellular organelle following expression of the exogenous polynucleotides.

According to still further features in the described preferred embodiments the exogenous polynucleotides are of bacterial origin.

According to still further features in the described preferred embodiments the exogenous polynucleotides include bacterial proB and proA coding sequences.

According to still further features in the described preferred embodiments the bacterial proB and proA coding sequences each include a leader sequence for targeting the enzymes expressed therefrom into the subcellular organelle of the plant.

According to still further features in the described preferred embodiments the exogenous polynucleotides are of plant origin.

According to still further features in the described preferred embodiments the exogenous polynucleotides each include a leader sequence for targeting the enzymes expressed therefrom into the subcellular organelle of the plant.

According to still further features in the described preferred embodiments the enzymes form a delta-pyrroline-5-carboxylate synthase (P5CS) complex.

According to still further features in the described preferred embodiments at least one of the exogenous polynucleotides encodes a mutant enzyme showing relative insensitivity to proline inhibition.

According to still further features in the described preferred embodiments the subcellular organelle is a chloroplast.

According to still further features in the described preferred embodiments the method alternatively or further comprising the step of downregulating within the plant at least one endogenous enzyme participating in proline catabolism.

According to still further features in the described preferred embodiments the at least one endogenous enzyme participating in proline catabolism is selected from the group consisting of proline dehydrogenase (PDh) and P5C-dehydrogenase (P5C-Dh).

According to still further features in the described preferred embodiments the step of downregulating within the plant at least one endogenous enzyme participating in proline catabolism is effected by a method selected from the group consisting of (a) deletion of a gene encoding the at least one endogenous enzyme responsible for the catabolism of proline; (b) mutation of the gene encoding the at least one endogenous enzyme responsible for the catabolism of proline; (c) transcriptional inactivation of the gene encoding the at least one endogenous enzyme responsible for the catabolism of proline; (d) antisense RNA mediated inactivation of transcripts of the gene encoding the at least one endogenous enzyme responsible for the catabolism of proline; and (e) translational inactivation of transcripts of the gene encoding the at least one endogenous enzyme responsible for the catabolism of proline.

According to still further features in the described preferred embodiments the environmental stress conditions are selected from the group consisting of high salinity, extreme temperature and drought.

The present invention successfully addresses the shortcomings of the presently known configurations by providing a plant with unprecedented proline content when grown under optimal growth conditions and which is therefore more adapted at growth under stress conditions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3 depicts a sequence alignment between the alfalfa PDh gene and it's corresponding cDNA.

FIG. 5a—Northern blot analysis of PDh mRNA levels in roots; alfalfa PDh cDNA and ribosomal DNA (18S) fragments were used as probes. FIG. 5b—proline content in roots. Bars represent the standard error of three replicates. FIG. 5c—Northern blot analysis of PDh mRNA levels in leaves. Sampling at identical times was practiced in order to eliminate differences associated with circadian rhythm.

FIGS. 6e-g depict the vectors which express the antisense PDh fragment. All the above vectors are binary vectors designed for *Agrobacterium* mediated transformation.

DESCRIPTION OF THE PREFERRED EMBODIMENTS

Figure 1:
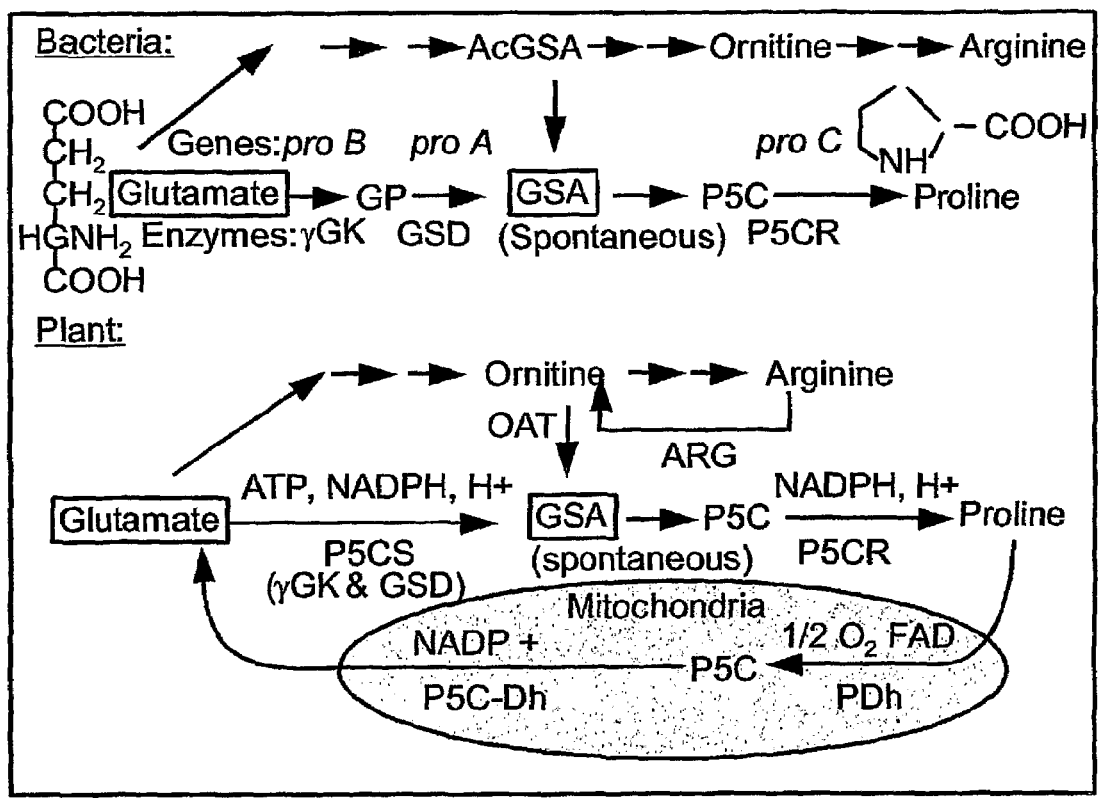
FIG. 1 is a schematic depiction of proline biosynthesis pathway in bacteria and plants indicating the genes and enzymes participating in the pathway. Abbreviations: AcGSA, N-actyl glutamyl semialdehyde; GSA, glutamic gamma-semialdehyde; GP, glutamyl phosphate; P5C, D1-pyrroline-5-carboxylate. Enzymes: ARG, Arginase; gamma-GK, gamma-Glutamyl Kinase; GSD, Glutamic gamma-Semialdehyde Dehydrogenase (also known as GPR); OAT, ornithine amino transferase; P5CS, P5C synthetase; P5CR, P5C reductase; PDh, Proline dehydrogenase; P5C-Dh, P5C dehydrogenase.

The present invention is of methods of generating plants tolerant of extreme environmental stress conditions. In particular, the generation of such plants according to the present invention, is effected by the over expression of enzymes involved in the biosynthesis of proline, preferably in combination with the downregulation of endogenous proline degrading enzymes. The present invention also relates to an alfalfa (*Medicago sativa*) gene including a novel stress sensitive promoter and encoding a novel proline dehydrogenase (oxidase) enzyme which catalyses the first step in plant proline degradation and as such, can be specifically targeted for downregulating proline degradation according to the present invention.

The principles and operation of the present invention may be better understood with reference to the accompanying descriptions.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

The proline level which accumulate in wild type plants during osmotic stress can reach up to two orders of magnitudes higher then normal levels of non stressed plants. For example, proline level in wheat plants subjected to environmental stress, are 195 folds higher than that of the same plants grown under optimal conditions; in tomato cell suspension culture this increase is approximately 319 folds higher than non-stressed cells; in a cell culture of a tobacco salt resistant strain (*Nicotiana sylvestris*) the proline level increase was found to be 46 fold higher than that of unstressed cultures (Delauney and Verma, 1993).

Thus, under environmental stress conditions the proline level in plant tissue increases by a substantial amount which could be as much as 319 times that of comparable unstressed plants.

These observations encouraged scientists to develop plants which are inherently characterized by elevated proline level, because such plants are expected to be more tolerant to environmental stress conditions.

Prior art attempts for increasing proline level in plants have failed to attain such a substantial increase. For example, the increase in the proline level of transgenic tobacco plants expressing the wild-type P5CS enzyme complex from Vigna plants maximized at 14 times that of wild type plants (Kishor et al., 1995). Results from other studies have demonstrated similar increase in proline level.

Although proline level increase effected by prior art methods can provide a plant some protection when subjected to environmental stress, it is believed that this increase is not sufficient either under extreme stress or prolonged periods of stress, and as such, to better protect a plant against stress conditions higher levels of proline must be accumulated therein.

Optimally, a method designed for expressing high level of proline in plants should increase the proline to levels close to a level found in wild type plants subjected to stress conditions, i.e., approximately 40-300 times higher than that of non-stressed plants.

Thus, it was a goal of the inventors of the present invention to devise a method of generating a plant which can accumulate proline to levels found in wild type plants subjected to stress conditions.

While reducing the present invention to practice, transgenic tobacco plants accumulating high levels of proline were generated. The increase in the proline level of these transgenic tobacco plants was up to 35 times in comparison with the wild type in mature plants and up to 109 times in comparison with the wild type in plant seedlings.

As is further detailed in the Examples section below, this increase in proline level, which is substantially higher than that demonstrated by prior art methods, was achieved by generating a transgenic plant which accumulates exogenous proline biosynthetic enzymes in the chloroplast, while preferably also expresses an antisense RNA which inactivates an endogenous proline degradation enzyme.

Thus, according to one aspect of the present invention, there is provided a method of generating a plant tolerant of an environmental stress condition, the method comprising the step of expressing within the plant exogenous polynucleotides encoding enzymes capable of catalyzing proline production.

As used herein, the phrase "environmental stress condition" refers to environmental conditions which are suboptimal for plant growth and/or development. Such conditions can be, for example, high salinity, suboptimal temperatures and drought, or any other environmental condition which is stressful to the plant and as such severely affects it's development or growth.

According to a preferred embodiment of the present invention, the enzymes capable of catalyzing proline production form a functional delta-pyrroline-5-carboxylate synthase (P5CS) enzyme complex following expression within the plant. This enzyme complex catalyses the first two steps in the conversion of glutamate into proline as is further described hereinabove.

While reducing the present invention to practice it was uncovered that targeting the enzymes capable of catalyzing proline production into a subcellular organelle, such as a chloroplast, leads to a higher increase of the proline level, as is compared to cytosolic targeting of the same enzymes.

Expression of proline biosynthesis enzymes in a subcellular organelle, such as the chloroplast, is of particular advantage over prior art approaches, since the chloroplast contains high concentrations of glutamate which is the main precursor to proline. In addition, locating proline biosynthesis within the chloroplast isolates the biosynthetic enzymes from various downregulative elements which are found in the plant cell cytosol, which is the location of the endogenous proline biosynthesis pathway. Furthermore, a plant produced by the method of the present invention synthesizes proline in two distinct locations in the cell, and as such is less prone to inhibitory effects which may arise from proline accumulation.

As such, according to the present invention the enzymes capable of catalyzing proline production, are preferably expressed in a manner so as to allow accumulation of the enzymes within a subcellular organelle of the plant. For example, in cases where the subcellular organelle is a DNA containing organelle such as a chloroplast or a mitochondrion, direct transformation of this DNA with exogenous polynucleotides encoding these enzymes can be effected. Further detail to transformations of DNA containing organelles is given hereinbelow.

Alternatively, and according to another preferred embodiment of the present invention, the enzymes are targeted into the subcellular organelle following expression of the exogenous polynucleotides in the cytosol. According to this embodiment the enzymes expressed include a leader or transit peptide which targets the expressed enzymes into a subcellular organelle. For example, the chloroplast targeting leader sequence of the Rubisco small subunit can be utilized to target the enzymes into the chloroplast. Further description to the Rubisco small subunit leader sequence is given in the Examples section. Other transit peptides are well known in the art. Mitochondrial, nuclear, chloroplast, or vacuolar signals target expressed protein correctly into the corresponding organelle through the secretory pathway, see, Von Heijne, Eur. J. Biochem. (1983) 133:17-21; Yon Heijne, J. Mol. Biol. (1986) 189:239-242; Iturriaga et al. The Plant Cell (1989) 1:381-390; McKnight et al, Nucl. Acid Res. (1990) 18:4939-4943; Matsuoka and Nakamura, Proc. Natl. Acad. Sci. USA (1991) 88:834-838. A recent book by Cunningham and Porter (Recombinant proteins from plants, Eds. C. Cunningham and A. J. R. Porter, 1998 Humana Press Totowa, N.J.) describe methods for the production of recombinant proteins in plants and methods for targeting the proteins to different compartments in the plant cell. In particular, two chapters therein (14 and 15) describe different methods of introducing targeting sequences that result in accumulation of recombinant proteins in compartments such as ER, vacuole, plastid, nucleus and cytoplasm. The book by Cunningham and Porter is incorporated herein by reference.

The exogenous polynucleotide sequences encoding the enzymes capable of converting glutamate to proline can be bacterial or plant polynucleotide sequences.

For example, the bacterial proB and proA coding sequences (GeneBank Accession No. x00786, for both, which are incorporated herein by reference), or the plant GK and GSD enzymes which form P5CS (for example, P5CS-1 and P5CS-2 from *M. sativa* GeneBank Accession Nos. X98421 and X98422 respectively, which are incorporated herein by reference) can be utilized by the present invention. Additional examples include, but are not limited to, Lycopersicon esculentum gamma-glutamyl kinase and gamma-glutamyl phosphate reductase (PRO1) (GeneBank Accession No. U27454), Saccharomyces cerevisiae gamma-glutamyl kinase (PRO1) gene (GeneBank Accession No. M85293) and gamma-glutamyl phosphate reductase (PRO2) gene (GeneBank Accession No U43565), Human pyrroline-5-carboxylate synthase (P5Cs) mRNA (GeneBank Accession No. U68758). Such sequences can be used either to directly transform a DNA containing organelle, or such coding sequences can each include a leader sequence for targeting the enzymes expressed therefrom into the subcellular organelle of the plant.

It will be appreciated that in order for the coding sequences to be expressed within the plant, such sequences must be fused to cis acting regulatory elements such as promoters, enhancers and the like. Further description of such regulatory sequences is given hereinbelow.

According to another preferred embodiment of the present invention, at least one of the exogenous polynucleotides encodes an enzyme showing relative insensitivity to proline (end-product) feed-back inhibition. An example to a plant derived proline biosynthetic enzyme (and the cDNA thereof) which is relatively insensitive to proline inhibition was described by Zhang et al., (1995), which is incorporated herein by reference. It will be appreciated in this respect that the proteins encoded by the bacterial proB and proA genes are inherently insensitivity to proline feed-back inhibition.

In addition, further increase in proline level can be generated by overexpressing OAT—ornithine amino transferase (GeneBank Accession No. L08400) in the transgenic plant of the present invention. The role of OAT in proline metabolism is outlined in FIG. 1.

To further increase proline level beyond that achieved by the overexpression of proline biosynthetic enzymes, as is described hereinabove, the method of the present invention further includes the step of downregulating within the plant at least one endogenous enzyme participating in the catabolism (degradation) of proline.

As used herein, the term "downregulation" refers to decreasing the expression or activity levels of an endogenous enzyme. Such a decrease can in the range of 10% or more and up to substantially 100% decrease of activity as is compared to the wild type level of activity, the latter value is in effect considered as total inactivation of the endogenous enzyme.

It will be appreciated in this respect that, since proline level in the cell is regulated by the activity of both biosynthetic (anabolic) and degradation (catabolic) enzymes, downregulation of degradation enzymes can further enhance the plants ability to accumulate proline in high levels.

As such according to another preferred embodiment of the present invention, downregulation of at least one endogenous enzyme responsible for the catabolism of proline such as, for example, proline dehydrogenase (PDh) (GeneBank accession No. D83025 incorporated herein by reference) or P5C-dehydrogenase (P5C-Dh), is effected.

According to preferred embodiments of the present invention, such downregulation is effected by a method, such as, but not limited to, (a) deletion of a gene encoding the at least one endogenous enzyme responsible for the catabolism of proline; (b) mutation of the gene encoding the at least one endogenous enzyme responsible for the catabolism of proline; (c) transcriptional inactivation of the gene encoding the at least one endogenous enzyme responsible for the catabolism of proline; (d) antisense RNA mediated inactivation of transcripts of the gene encoding the at least one endogenous enzyme responsible for the catabolism of proline; and (e) translational inactivation of transcripts of the gene encoding the at least one endogenous enzyme responsible for the catabolism of proline.

Thus, for example, gene knock-in or gene knock-out constructs including sequences homologous with the gene encoding the endogenous enzyme responsible for the catabolism of proline can be generated and used to insert an ancillary sequence into the coding sequence of the enzyme encoding gene, to thereby inactivate this gene.

These construct preferably include positive and negative selection markers and may therefore be employed for selecting for homologous recombination events. One ordinarily skilled in the art can readily design a knock-in/knock-out construct including both positive and negative selection genes for efficiently selecting transformed plant cells that underwent a homologous recombination event with the construct. Such cells can then be grown into full plants. Standard methods known in the art can be used for implementing knock-in/knock out procedure. Such methods are set forth in, for example, U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson, Methods in Enzymology, 194: 251-270, 1991; Capecchi, Science 244:1288-1292, 1989; Davies et al., Nucleic Acids Research, 20 (11) 2693-2698, 1992; Dickinson et al., Human Molecular Genetics, 2(8): 1299-1302, 1993; Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742-750 1991; Jakobovits et al., Nature, 362:255-261 1993; Lamb et al., Nature Genetics, 5: 22-29, 1993; Pearson and Choi, Proc. Natl. Acad. Sci. USA, 1993, 90:10578-82; Rothstein, Methods in Enzymology, 194:281-301, 1991; Schedl et al., Nature, 362: 258-261, 1993; Strauss et al., Science, 259:1904-1907, 1993, WO 94/23049, WO93/14200, WO 94/06908 and WO 94/28123 also provide information.

At the transcription level, expressing antisense or sense oligonucleotides that bind to the genomic DNA by strand displacement or the formation of a triple helix, may prevent transcription. At the transcript level, expression of antisense oligonucleotides that bind target mRNA molecules lead to the enzymatic cleavage of the hybrid by intracellular RNase H or prevention of translation thereof into a protein. In this case, by hybridizing to the targeted mRNA, the oligonucleotides provide a duplex hybrid recognized and destroyed by the RNase H enzyme or which prevents binding to ribosomes. In addition the use of ribozyme sequences linked to antisense oligonucleotides can also facilitate target sequence cleavage by the ribozyme. Alternatively, such hybrid formation may lead to interference with correct RNA splicing into messenger RNA. As a result, in all cases, the number of the target mRNA intact transcripts ready for translation is reduced or eliminated. At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs.

It will be appreciated that the antisense strategies described above preferably utilize antisense oligonucleotides which are hybridizable to highly conserved regions unique to proline degradation enzymes such that a wide spectrum of such enzymes can be inactivated via a single construct. An example to such a highly conserved region is given in the Examples section which follows.

Although downregulation of an endogenous enzyme responsible for the catabolism of proline is preferably effected in transgenic plants expressing biosynthetic enzymes in the chloroplast (as described above), the downregulation approach can also be implemented independently of chloroplastic expression of biosynthetic enzymes although such an approach can only increase proline by eight folds as compared to wild type plants.

As described hereinabove, the method according to the present invention can be utilized to generate a transgenic plant which can accumulate a high level of proline and as such be tolerant of an environmental stress condition.

According to the present invention, such a plant, when mature, displays a level of proline which is at least fifteen times higher, preferably at least twenty times higher, more preferably at least twenty five times higher, most preferably at least forty to sixty times higher than a non-transgenic isogenic plant, wherein both plants are grown under optimal conditions which result in a lowest proline content in the non-transgenic plant. Such conditions include sufficient water supply, suitable concentration of various essential minerals, optimal temperature, optimal photoperiods, etc.

Alternatively, such a plant when at a seedling stage, displays a level of proline which is at least thirty times higher, preferably at least forty times higher, more preferably at least sixty times higher, most preferably at least eighty to one hundred and twenty times higher than a non-transgenic isogenic plant, wherein both plant seedlings are cultivated under normal environmental conditions.

In any case, due to the high levels of proline accumulated therein, the plant generated by the method of the present invention is well tolerant of environmental stress conditions. It will be appreciated that the method of the present invention is particularly advantageous for growing plants under environmental stress conditions, since proline is accumulated to very high levels in seedlings which are considered more affected by environmental stress conditions as is compared to mature plants.

Several nucleic acid transformation methods can be used to implement the method of generating stress tolerant plants according to the present invention.

For effecting plant transformation, the exogenous polynucleotides which encode enzymes capable of catalyzing proline production are preferably included within a nucleic acid construct or constructs which serve to facilitates the introduction of the exogenous polynucleotides into plant cells or tissues and the expression of the enzymes in the plant.

Thus, a first nucleic acid construct according to the present invention includes a first polynucleotide region encoding a first enzyme participating in the biosynthesis of proline and optionally a second polynucleotide region encoding a second enzyme participating in the biosynthesis of proline.

Since the expression product of this construct preferably accumulates in a subcellular organelle such as a chloroplast in cases where this construct is transformed into the genome of a plant and not the DNA of DNA containing organelle, each of the first and second polynucleotide regions also includes a leader peptide sequence preferably at the 5' end of the polynucleotide coding region and in translational fusion (in frame) thereto.

According to another embodiment of the present invention the nucleic acid construct further includes a third polynucleotide region which is capable of inactivating a plant endogenous gene which encodes an enzyme participating in the degradation of proline.

Alternatively and preferably the third polynucleotide region which functions in downregulating the expression of the endogenous gene, via, for example antisense RNA is provided on a second construct.

The nucleic acid constructs according to the present invention are utilized to express in either a transient or preferably a stable manner both the exogenous polynucleotides and the polynucleotide which functions in downregulating the expression of the endogenous gene (also termed hereinunder as construct "inserts") within a whole plant, defined plant tissues, or defined plant cells.

Thus, according to a preferred embodiment of the present invention, the nucleic acid constructs further include a promoter for regulating the expression of insert(s) thereof. It will be appreciated that constructs including two expressible inserts preferably include an individual promoter for each insert, or alternatively such constructs can express a single transcript chimera including both insert sequences from a single promoter. In such a case, the chimeric transcript includes an IRES sequence between the two insert sequences such that the downstream insert can be translated therefrom.

Numerous plant functional expression promoters and enhancers which can be either tissue specific, developmentally specific, constitutive or inducible can be utilized by the constructs of the present invention, some examples are provided hereinunder.

As used herein in the specification and in the claims section that follows the phrase "plant promoter" or "promoter" includes a promoter which can direct gene expression in plant cells (including DNA containing organelles). Such a promoter can be derived from a plant, bacterial, viral, fungal or animal origin. Such a promoter can be constitutive, i.e., capable of directing high level of gene expression in a plurality of plant tissues, tissue specific, i.e., capable of directing gene expression in a particular plant tissue or tissues, inducible, i.e., capable of directing gene expression under a stimulus, or chimeric, i.e., formed of portions of at least two different promoters.

Thus, the plant promoter employed can be a constitutive promoter, a tissue specific promoter, an inducible promoter or a chimeric promoter.

Examples of constitutive plant promoters include, without being limited to, CaMV35S and CaMV19S promoters, FMV34S promoter, sugarcane bacilliform badnavirus promoter, CsVMV promoter, *Arabidopsis* ACT2/ACT8 actin promoter, *Arabidopsis* ubiquitin UBQ1 promoter, barley leaf thionin BTH6 promoter, and rice actin promoter.

Examples of tissue specific promoters include, without being limited to, bean phaseolin storage protein promoter, DLEC promoter, PHSβ promoter, zein storage protein promoter, conglutin gamma promoter from soybean, AT2S1 gene promoter, ACT11 actin promoter from *Arabidopsis*, napA promoter from *Brassica napus* and potato patatin gene promoter.

The inducible promoter is a promoter induced by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

Preferably the promoter utilized by the present invention is a strong constitutive promoter such that over expression of the construct inserts is effected following plant transformation.

As used herein the term "overexpression" refers to expressing a protein to a level higher than that found naturally in the plant.

According to the present invention, over expression can also be effected by transforming the plant with a high copy number of the nucleic acid, or by utilizing cis acting sequences which stabilize the resultant transcript and as such decrease the degradation or "turn-over" of such a transcript.

Each of the constructs according to the present invention preferably ether includes an appropriate and unique selectable marker, such as, for example, an antibiotic resistance gene. In a more preferred embodiment according to the present invention the constructs further include an origin of replication.

Any of the constructs according to the present invention can be a shuttle vector, which can propagate both in *E. coli* (wherein the construct comprises an appropriate selectable marker and origin of replication) and be compatible for propagation in cells, or integration in the genome, of a plant. Any of the constructs according to the present invention can be, for example, a plasmid, a bacmid, a phagemid, a cosmid, a phage, a virus or an artificial chromosome.

Thus, the method of the present invention utilizes two construct types. A first construct is utilized for the expression of enzymes which are capable of catalyzing proline production, wherein a second construct is utilized for the inactivation, via, for example, antisense RNA, or gene knock-in/knock-out (further described hereinabove) of an endogenous enzyme participating in proline degradation.

It will be appreciated that both construct types can be co-transformed into the same plant using different selection markers in each construct type. Alternatively the first construct type can be introduced into a first plant while the second construct type can be introduced into a second isogenic plant, following which the transgenic plants resultant therefrom can be crossed and the progeny selected for double transformants. Further self-crosses of such progeny can be employed to generate lines homozygous for both constructs.

There are various methods of introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct in which case these sequences are not inherited by a progeny of the plant.

In addition, several method exist in which a nucleic acid conrtruct can be directly introduced into the DNA of a DNA containing organelle such as a chloroplast.

There are two principle methods of effecting stable genomic integration of exogenous sequences such as those included within the nucleic acid constructs of the present invention into plant genomes:

(i) *Agrobacterium*-mediated gene transfer: Klee et al. (1987) Annu. Rev. Plant Physiol. 38:467486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Transient expression methods which can be utilized for transiently expressing the isolated nucleic acid included within the nucleic acid construct of the present invention include, but are not limited to, microinjection and bombardment as described above but under conditions which favor transient expression, and viral mediated expression wherein a packaged or unpackaged recombinant virus vector including the nucleic acid construct is utilized to infect plant tissues or cells such that a propagating recombinant virus established therein expresses the non-viral nucleic acid sequence.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

According to another aspect of the present invention there is provided an isolated nucleic acid comprising a genomic, complementary or composite polynucleotide sequence encoding a polypeptide at least 65%, at least 70%, at least 75%, at least 80%, at least 85%, at least 90%, at least 95%, 97-100% homologous (similar+identical amino acids) to SEQ ID NO:5 as determined using the BestFit software of the Wisconsin sequence analysis package, utilizing the Smith and Waterman algorithm, where gap creation penalty equals 8 and gap extension penalty equals 2.

The polypeptide according to this aspect of the present invention is preferably functional as a proline dehydrogenase.

As used herein in the specification and in the claims section that follows, the phrase "complementary polynucleotide sequence" includes sequences which originally result from reverse transcription of messenger RNA using a reverse transcriptase or any other RNA dependent DNA polymerase. Such sequences can be subsequently amplified in vivo or in vitro using a DNA dependent DNA polymerase.

As used herein in the specification and in the claims section that follows, the phrase "genomic polynucleotide sequence" includes sequences which originally derive from a chromosome and reflect a contiguous portion of a chromosome.

As used herein in the specification and in the claims section that follows, the phrase "composite polynucleotide sequence" includes sequences which are at least partially complementary and at least partially genomic.

As used herein the terms "homology" or "homologous" refer to the resemblance between compared polypeptide sequences as determined from the identity (match) and similarity (amino acids of the same group) between amino acids which comprise these polypeptide sequences.

Preferably, the isolated nucleic acid according to this aspect of the present invention is hybridizable with SEQ ID NOs:4 or 6 under moderate to stringent hybridization conditions.

Hybridization under moderate hybridization conditions is effected by a hybridization solution containing 10% dextrane sulfate, 1 M NaCl, 1% SDS and $5 \times 10^6$ cpm $^{32}$P labeled probe, at 65° C., with a final wash solution of 1×SSC and 0.1% SDS and final wash at 55 to 65, preferably 60° C., whereas, hybridization under stringent hybridization conditions is effected by a hybridization solution containing 10% dextrane sulfate, 1 M NaCl, 1% SDS and $5 \times 10^6$ cpm $^{32}$P labeled probe, at 65° C., with a final wash solution of 0.1×SSC and 0.1% SDS and final wash at 55 to 65, preferably 60° C.

Alternatively or additionally, the isolated nucleic acid comprises a genomic, complementary or composite polynucleotide sequence at least 60% at least 65%, at least 70%, at least 75%, at least 80%, at least 85%, at least 90%, at least 95%, 97-100% identical with SEQ ID NOs:4 or 6 as determined using the BestFit software of the Wisconsin sequence analysis package, utilizing the Smith and Waterman algorithm, where gap weight equals 50, length weight equals 3, average match equals 10 and average mismatch equals −9.

According to a preferred embodiment of the present invention the isolated nucleic acid is set forth in SEQ ID NOs:4 or 6 or a contiguous single (any strand) or double stranded portion thereof of at least 10, preferably at least 20, more preferably at least 30, more preferably at least 40, more preferably at least 50, more preferably at least 60, more preferably at least 70, more preferably at least 80 bases or base pairs, respectively.

According to another preferred embodiment of the present invention the polypeptide according to this aspect of the present invention is as set forth in SEQ ID NO:5.

The nucleic acid sequence of this aspect of the present invention may be amplified by known nucleic acid amplification protocols, such as, but not limited to, the polymerase chain reaction (PCR). To this end, there is provided a pair of oligonucleotides each of at least 17, preferably at least 18, more preferably between 19 and 25, still preferably, at least 26, say, 27-50 bases in length, which are specifically hybridizable with the isolated nucleic acid described herein in an opposite orientation, so as to direct exponential amplification of a portion thereof in a nucleic acid amplification reaction, thereby obtaining a nucleic acid amplification product. The melting temperature (Tm) of the oligonucleotides of the pair of nucleotides is preferably selected similar so as to enable hybridization thereof to target sequences under similar conditions. Such melting temperature can be estimated in advance using an appropriate software, such as, but not limited to the OLIGO software. Sequence mutated or modified oligonucleotides can be used for various purposes, such as, but not limited to, the introduction of mutation(s) or other sequence alterations in the resulting sequence.

The isolated nucleic acid according to this aspect of the present invention or any portion thereof can be included in a nucleic acid construct in a sense or antisense orientation.

This construct can further include a promoter for expressing either a sense or an antisense strand of the isolated nucleic acid or a portion thereof.

It will be appreciated that since the nucleic acid according to this aspect of the present invention encodes a proline dehydrogenase which participates in proline degradation, sequence regions from this isolated nucleic acid can be used to inactivate endogenous proline dehydrogenase gene via gene knock-in/knockout, or via antisense RNA, as further described hereinabove.

As such the construct according to this aspect of the present invention which includes the isolated nucleic acid or a portion thereof which is at least 10 base pairs long, at least 20 base pairs long, at least 30-50 base pairs long, at least 60-80 base pairs long, at least 100-200 base pairs long, and which is provided in an antisense orientation to the promoter can be introduced into a plant via methods described above.

Thus, when such a construct is expressed within a plant cell, an antisense molecule is generated. Such an antisense molecule is capable of specifically hybridizing with either a proline dehydrogenase gene or a transcript thereof under physiological conditions.

It will be appreciated that the construct can also include a ribozyme sequence transcriptionally fused to the isolated nucleic acid coding sequence.

Alternatively, a gene knock-in/knock-out construct including sequences of the isolated nucleic acid of this aspect of the present invention can be constructed and utilized as described hereinabove.

Another aspect of the present invention relates to a recombinant protein. According to one embodiment, the recombinant protein comprises a polypeptide sequence at least 65%, at least 70%, at least 75%, at least 80%, at least 85%, at least 90%, at least 95%, 97-100% homologous to SEQ ID NO:5 as determined using the BestFit software of the Wisconsin sequence analysis package, utilizing the Smith and Waterman algorithm, where gap creation penalty equals 8 and gap extension penalty equals 2.

According to another embodiment, the recombinant protein comprises a polypeptide sequence encoded by a polynucleotide hybridizable with SEQ ID NOs:4 or 6 under moderate to stringent hybridization conditions According to still another embodiment, the recombinant protein comprises a polypeptide sequence encoded by a polynucleotide at least 60%, at least 65%, at least 70%, at least 75%, at least 80%, at least 85%, at least 90%, at least 95%, 97-100% identical with SEQ ID NOs:4 or 6 as determined using the BestFit software of the Wisconsin sequence analysis package, utilizing the Smith and Waterman algorithm, where gap weight equals 50, length weight equals 3, average match equals 10 and average mismatch equals −9.

Preferably, the recombinant protein comprises a polypeptide sequence as set forth in SEQ ID NO:5.

The recombinant protein according to this aspect of the present invention is preferably a proline dehydrogenase enzyme.

According to another aspect of the present invention there is provided an isolated nucleic acid comprising a polynucleotide sequence encoding a plant promoter, the isolated nucleic acid being hybridizable with SEQ ID NOs:7 or 8 under moderate to stringent hybridization conditions.

Alternatively or additionally, the isolated nucleic acid according to this aspect of the present invention, is at least 60%, at least 65%, at least 70%, at least 75%, at least 80%, at least 85%, at least 90%, at least 95%, 97-100% identical with SEQ ID NOs:7 or 8 as determined using the BestFit software of the Wisconsin sequence analysis package, utilizing the Smith and Waterman algorithm, where gap weight equals 50, length weight equals 3, average match equals 10 and average mismatch equals −9.

Preferably the isolated nucleic acid of this aspect of the present invention is as set forth in SEQ ID NOs:7 or 8.

It will be appreciated that the isolated nucleic acid of this aspect of the present invention can be amplified via PCR or any other nucleic acid amplification protocol, as is further described hereinabove.

As is further described in the Examples section below, the isolated nucleic acid of this aspect of the present invention encodes a promoter which is strongly downregulated shortly after the imposition of salt stress in a plant, and strongly induced shortly after the removal of the salt stress from the plant.

Since the isolated nucleic acid of this aspect of the present invention encodes a regulatable or inducible plant promoter it can be utilized for expression of polynucleotides for a variety of purposes.

Thus, this aspect of the present invention also provides a nucleic acid construct which includes the isolated nucleic acid which functions as an inducible promoter.

Environmental growth conditions which subject a plant to, for example, a water source which contains a 25 mM concentration of NaCl, induces salt stress thereon. In order to justify the logic of osmotic adjustment by accumulation of proline as osmolite, the level of accumulation in the plant should be around 25 mM to counteract the low water potential of the environment. During salt stress proline accumulates mainly in the cytoplasm (Leigh et al., 1981; Ketchum et al., 1991) and salts accumulates in the vacuole in which enzymatic activity is extremely low (Taiz and Zeiger, 1998). This mechanism generates the water balance inside the cell. The vacuole occupies 90-95% of the cell volume while the cytoplasm occupies about 5% of the cell volume (Taiz and Zeiger, 1998). Free proline level in total fluid from leaves of wild type mature tobacco plants growing in normal conditions is about 0.04 mM±0.02, while the actual proline concentration in the cytoplasm of such plants is 0.8 mM (0.04×20). The increase in proline level in transgenic tobacco plants that were developed while reducing the present invention to practice was 35 to 109 folds higher than that of wild type plants. This translates to an actual cytoplasmic proline concentration of 28 mM which is more than sufficient in providing osmotic stress protection to a plant generated according to the teachings of the present invention.

Thus the method according to the present invention utilizes a combination of proline anabolism upregulation and proline catabolism downregulation to enable the generation of plants which are more adapted to growth and development under environmental stress conditions than plants generated by prior art methods.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Plant growth and stress treatments: Alfalfa (*Medicago sativa*) seedlings were grown hydrophonically in a greenhouse, in 5 L liquid medium containing 123 mg/L $MgSO_4$, 44 mg/L $K_2SO_4$, 5 mg/L Sequestrenel38-Fe, 86 mg/L $CuSO_4.2H_2O$, 57 mg/L $K_2HPO_4.3H_2O$, 303 mg/L $KNO_3$ and microelements including: 932 mg/L KCl, 386 mg/L $H_3BO_3$, 211 mg/L $MnSO_4$, 94 mg/L $ZnSO_4.7H_2O$, 31 mg/L $CuSO_4.5H_2O$, 0.18 mg/L $CuCl.6H_2O$, 25 mg/L $Na_2MoO_4.2H_2O$.

Following three weeks of growth under light conditions of 16-h fluorescent light and 8-h dark, the seedlings were grown in a fresh batch of the above described growth medium including 170 mM NaCl. Root and shoot samples were collected at different time periods, immediately frozen in liquid nitrogen and stored at −70° C.

DNA modification and cloning: Plasmid DNA was prepared by the High Pure Plasmid Isolation kit (Boehringer-Mannheim, Indianapolis, Ind., USA) according to the manufacturer's protocol. Digestion with restriction enzymes was carried out according to the manufacturer's recommendations (New England Biolabs, Beverly, Mass., USA; Stratagene, LaJolla, Calif., USA; MBI Fermentas, Graiciuno, Lithuania) and restriction fragments were separated by agarose gel electrophoresis and visualized by ethidium bromide staining as described by Sambrook et al. (1989). Blunting of the 5' and 3' DNA protruding ends, dephosphorylation of the 5' end using calf intestinal alkaline phosphatase (Boehringer-Mannheim, Indianapolis, Ind., USA) and ligation were all performed as described by Sambrook et al. (1989).

Bacterial transformation: A portion of the ligation reaction including 10 to 100 ng of vector DNA was introduced into *E. coli* by the rubidium chloride method, as described by Hanahan, (1983). The transformed bacteria were selected on LB-agar (2%) plates containing 100 mg/L ampicillin. Bacterial colonies containing recombinant plasmids were identified by blue/white selection and by restriction digestion patterns of purified plasmids, as described by Sambrook et al. (1989).

PCR Amplification of alfalfa PDh: Total DNA or cDNA from alfalfa seedlings was used as a template for PCR amplification, using the PWO proofreading DNA polymerase (Boelringer-Mannheim, USA) or Ex-Taq (TakaRa, Gennevillier, France). Amplification and cloning of the first 0.4 Kb cDNA fragment of alfalfa PDh served as the basis for further cloning of a full length cDNA clone. The amplification of the 0.4 Kb PDh fragment was carried out with degenerate PCR primers corresponding to the margins of the conserved PDh region. This highly conserved region was identified by a multiple sequence alignment performed on the PDh protein sequences of *E. coli*, yeast, *Arabidopsis, Drosophila*, mouse and human. PCR amplification was performed using 50 ng total cDNA from alfalfa seedlings as a template and 600 pmoles of the forward primer 5'-GT-TYAARYTIGTIAGRGGIGCHTA-3' (SEQ ID NO:1) and the reverse primer 5'-CTCRTAIGCICKICKIARIARRTA-3' (SEQ ID NO:2). Following denaturation for 3.5 min at 94° C., 36 amplification cycles of 30 sec at 94° C., 1 min at 45° C. and 1 min at 72° C. were applied to the sample in a PTC-100 Programmable Thermal Controller (MJ Research Inc. USA). The resultant PCR product was gel purified, cloned into pUC57 (MBI Fermentas, Graiciuno, Lithuania) and sequenced.

DNA sequence analysis: Computer analysis of nucleotide and amino acid sequences was carried out using Bestfit, Gap, Assemble, Pileup, Lineup and Prettybox software modules of the GCG/EGCG package of the University of Wisconsin, USA.

Southern blot analysis: Total DNA was isolated from leaves of tobacco, alfalfa, tomato and potato plants. For Southern blot analysis, 20 mg DNA was digested with SphI or Bg/II, separated on a 1% agarose gel in Tris-acetate (TAE) buffer and blotted onto a Hybond-N+ membrane (Amersham, UK). The membrane was hybridized with a $^{32}$P-0.4 Kb PCR fragment of PDh cDNA labeled by random priming. Hybridization was carried out at 55° C. in 0.263 M $Na_2HPO_4$, 1% (w/v) BSA, 7% (w/v) SDS and 1 mM EDTA. Washes were performed once for 20 min at 60° C. with the following solutions: (1) 0.263 M $Na_2HPO_4$; 1% SDS (2) 2×SSC; 1% SDS (3) 1×SSC; 0.1% SDS.

Determination of PDh transcript levels by Northern blot analysis: Total RNA was isolated from salinized and control *Medicago saliva* roots and shoots using the Trizol-Reagent kit (GIBCO, BRL, USA). For evaluation of is the overall level of PDh transcripts by Northern analysis, denatured samples of 10 mg total RNA were loaded onto a 1% agarose gel, blotted onto a nylon membrane (Hybond N, Amersham, UK), and hybridized either with $^{32}$P-0.4 Kb PCR fragment of PDh cDNA or with a 1-Kb tomato $^{32}$P-rDNA fragment. The blots were washed once with 2×SSC, 0.1% (w/v) SDS at 65° C. for 20 min, and once with 1×SSC, 0.1% (w/v) SDS at 65° C. for 20 min and exposed to either X-ray film (Fujifilm, Fuji, Japan) with an intensifying screen at −70° C. or a Phosphor-Imager screen. The Phosphor-Imager Program (Fujix BAS 1500, Fuji, Japan) was used for radioactivity quantification.

Construction of the translational fusions between the RUBISCO small subunit transit peptide and the bacterial enzyme GK or GPR: The 5' sequence of the pea rbcS-3A gene, coding for the RUBISCO small subunit transit peptide (SEQ ID NO:3), which controls the protein uptake into the chloroplast, was translationally fused to the 5' end of each of the genes encoding the bacterial enzymes GK and GPR. A unique SphI restriction site found in this region of the rbcS-3A was digested and blunted with T4 DNA polymerase. A unique NdeI restriction site comprising the ATG translation initiation codon was introduced by PCR mutagenesis to the 5' end of the *E. coli* GK and GPR coding regions. This NdeI site was blunted with T4 DNA polymerase and ligated to the blunted rbcS-3A transit peptide segment.

Production of transgenic tobacco by Agrobacterium tumefaciens-mediated transformation: The plasmid vectors carrying either GK (GeneBank Accession No. X00786), GPR (GeneBank Accession No. X00786) or the 0.4 Kb PDh (nucleotide coordinates 1110-1494 on Alfalfa PDh cDNA sequence) segment in an antisense orientation were mobilized from *E. coli* SM10 into the *Agrobacterium tumefaciens* strain GV3101-pMP90RK (Koncz et al., 1989) by bi-parental transconjugation. Tobacco leaf disc transformation was performed as follows: the *A. tumefaciens* strain harboring the desired plasmid was incubated in 50 ml LB supplemented with 100 mg/L rifampicin, 25 mg/L gentamycin, 100 mg/L carbenicillin for 72 hr at 28° C. The stationary phase culture was centrifuged for 15 min at 6,000×g and the pellet was re-suspended in MS medium (SIGMA, ST. LOUIS, USA) to a final density of 0.5 $A_{600}$. Leaf discs were excised from young leaves of axenically grown tobacco (*Nicotiana tabacum*, NN), cut into 1 cm squares and wounded. Following wounding the tissue was incubated in 10 ml of a re-suspended *A. tumefaciens* culture for 1 hour and put onto MS medium plates containing 0.8% agar, 30 g/L sucrose, 2 mg/L kinetin and 0.8 mg/L IAA for 2 days at 25° C. under light conditions of 16 hour fluorescent light illumination period followed by an 8 hour dark period.

Two days later, the leaf discs were transferred onto fresh MS medium plates containing 0.8% agar, 30 g/L sucrose, 2 mg/L kinetin, 0.8 mg/L IAA, 500 mg/L claforan and 100 mg/L kanamycin or 15 mg/L hygromycin or both, depending on the combination of the binary plasmid vectors used in each transformation.

The leaf discs were transferred onto similar fresh medium every two weeks until regenerated shoots could be observed. The putative transgenic shoots were excised and transferred to MS medium plates containing 0.8% agar, 500 mg/L claforan and 100 mg/L kanamycin or 15 mg/L hygromycin or both. This medium was replaced every 2 weeks until roots developed.

The formation of roots by the excised shoots in the presence of kanamycin or hygromycin was an indication that the plants have been successfully transformed with the desired plasmid or plasmids. Small plantlets of approximately 1 to 2 cm in length were removed from the media and transplanted in soil containing pots covered with polyethylene bags for several days to one week to allow the plants to adjust to the soil and altered humidity conditions. Transformed tobacco plants were grown in soil at 25° C. under 16-h fluorescent light-8-h dark photoperiods.

Western blot analysis: Plant tissues were homogenized in 50 mM Tris-HCl buffer (pH 7), immediately mixed with equal volume of ×2 SDS-PAGE sample buffer and boiled for 10 minutes. Protein extracts were separated by SDS-PAGE using 12% (w/v) acrylamide gels, and then electro-transferred to PVDF membranes. Western blot analyses were performed using polyclonal antibodies raised in rabbit against denatured GK or GPR proteins.

Estimation of free proline content in plants: Proline content was measured in 1 g samples of root or shoot tissue using the Ninhydrin method previously described by Bates et al. (1973). Briefly, the samples were homogenized in 10 ml of 3% (w/v) sulfosalycilic acid and filtered through 3 mm Whatmann filter. A 3 ml sample of the filtrate was mixed with 3 ml of glacial-acetic acid and 3 ml of Ninhydrin solution [4.16% (w/v)]. Three volumes of the Ninhydrin—glacial-acetic acid solution were combined with 2 volumes of ortho-phosphoric acid and boiled for 1 hr. The resulting colored substance was extracted with 3 ml toluene and the absorbence at 520 nm was measured by a spectrophotometer.

Example 1

Characterization of the Proline Insensitive Enzyme GK74

Figure 2:
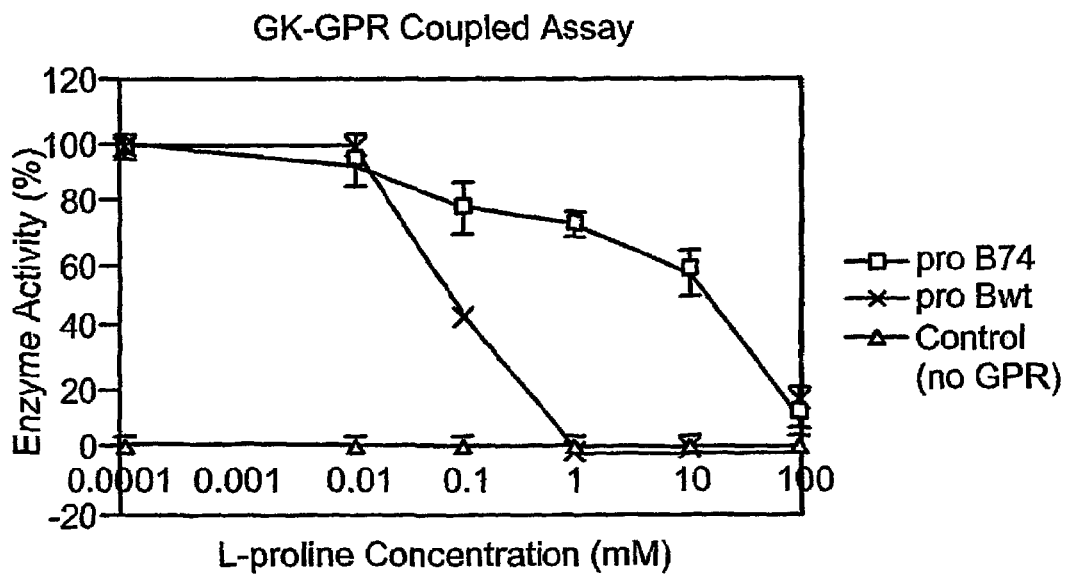
FIG. 2 is a graph depicting the effect of L-proline on GK and GPR activity as measured by a coupled assay. The enzymes were over expressed in *E. coli* and then assayed in vitro. Bars represent standard errors of four replicates.

A bacterial protein biosynthesis enzyme, termed GK74 (proB74 gene product), was evaluated as to the capacity to maintain its enzymatic activity in the presence of GPR and high proline concentrations as compared to a plant derived GK enzyme. The assay was carried out by over-expressing either plant GK (encoded by proBwt GeneBank Accession No. X00786) or bacterial GK74 encoded by proB74 (Csonka et al., 1988) along with GPR (GSD) in *E. coli* and performing GK-GPR coupled assays in vitro (FIG. 2). The results of these assays show that GK74 is indeed two order of magnitude less sensitive to proline as compared to the plant wild type GK. Consequently, the proline indifferent GK74 was considered as a good candidate for generating plants with high proline level.

There are several other advantages to using GK74 (proB74) instead of the plant GK (proBwt) gene. The bacterial genes are not co-suppressed by chromosomal homologues in the transformed plants and the introduced bacterial enzymes would not be recognized and inhibited by the P5CS (GK+GPR) inhibitor present in plant roots (Zhang et al., 1995).

In addition, by targeting GK74 and GPR to the chloroplast an interaction between GK74 and free proline that accumulates in the cytosol can be traversed thereby preventing feedback inhibition of GK74 even in the presence of very high concentrations of proline in the cell cytosol.

Example 2

A Novelfull Length Gene and the Corresponding cDNA Encoding PDh in Alfalfa

Amplification and Sequence Analysis of the Alfalfa PDh cDNA: Two different full-length PDh cDNAs were amplified as described above in the materials and methods section. The amplified PDh cDNAs were cloned and sequenced. Multiple alignment of both sequences and that of the PDh led to the elimination of mismatches between the two sequences resulting from point mutations introduced by the Reverse Transcriptase during cDNA synthesis, Taq polymerase substitution during PCR amplification or sequencing mistakes. The alfalfa PDh cDNA sequence (SEQ ID NO:4) exhibited 57% identity with the Arabidopsis PDh (Kiyosue et, al. 1996) at the DNA level. The translated protein sequence (SEQ ID NO:5) of the alfalfa PDh cDNA sequence displayed a 56% identity and 65% similarity with the Arabidopsis PDh protein sequence.

Figure 4:
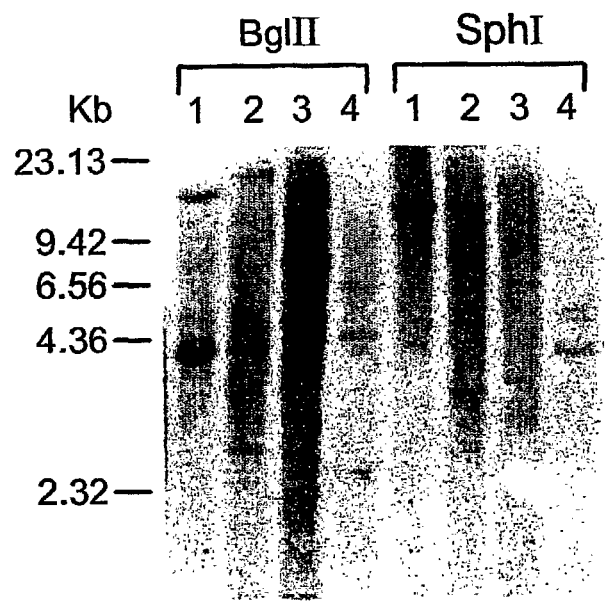
FIG. 4 is an image depicting a Southern-blot analysis of total DNA from tobacco (lane 1), alfalfa (lane 2), potato (lane 3) and tomato (lane 4) digested with BglII or SphI. The blot was probed with the 0.4 Kb fragment of alfalfa PDh representing the highly conserved region.

Amplification and Sequence Analysis of the Alfalfa PDh Gene: A 2.6 Kb amplified fragment representing most of the PDh gene was cloned and sequenced (SEQ ID NO:6). Sequence analysis showed the presence of a major intron, 0.57 Kb long, and two additional smaller introns (FIG. 3). Hybridization, under relatively stringent conditions, of tobacco, tomato, potato and alfalfa genomic DNA, with the highly conserved 0.4 Kb cDNA fragment of alfalfa PDh, demonstrated the existence of sequence homology (FIG. 4). These hybridization results showed that the 0.4 Kb cDNA fragment from alfalfa PDh could serve as a tool for heterologous anti-sense inactivation of PDh transcription in various plants.

Two different fragments containing the promoter regions upstream to the predicted transcription start site of the PDh mRNA of two distinct alfalfa PDh genes were cloned by the Inverse-PCR strategy. The first, consisting of a 722 bp region (SEQ ID NO:7), shared 94% identity with the second promoter region which includes 1439 bp (SEQ ID NO:8).

Figure 5A:
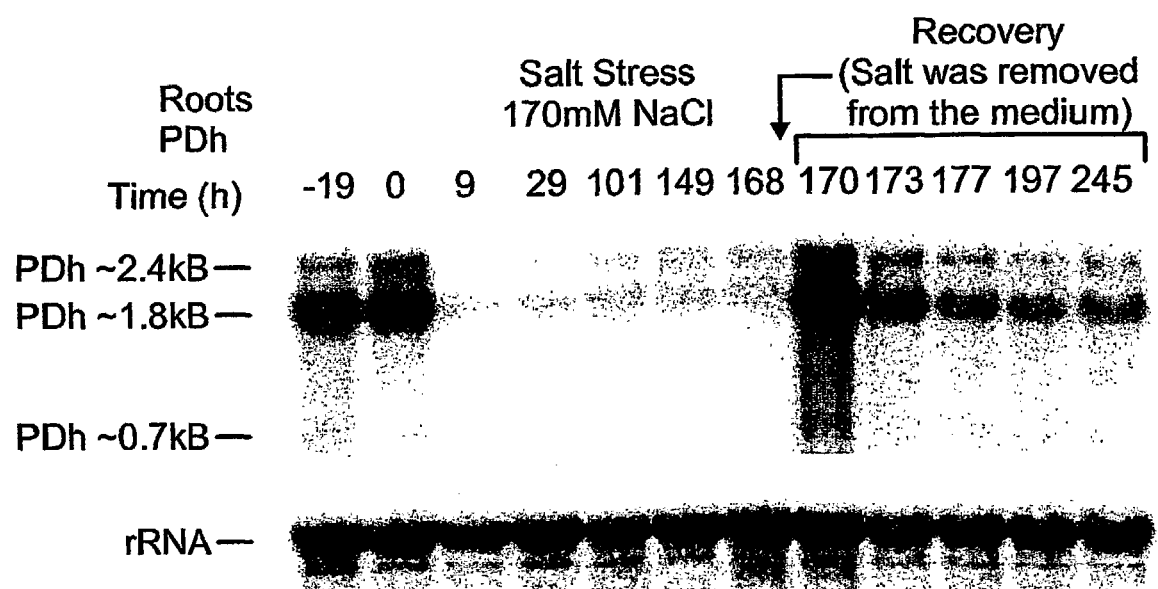
FIGS. 5a-c are images depicting PDh mRNA levels and free Proline level in roots and leaves of alfalfa seedlings during salt stress (170 mM NaCl), imposition and recovery.
Figure 5B:
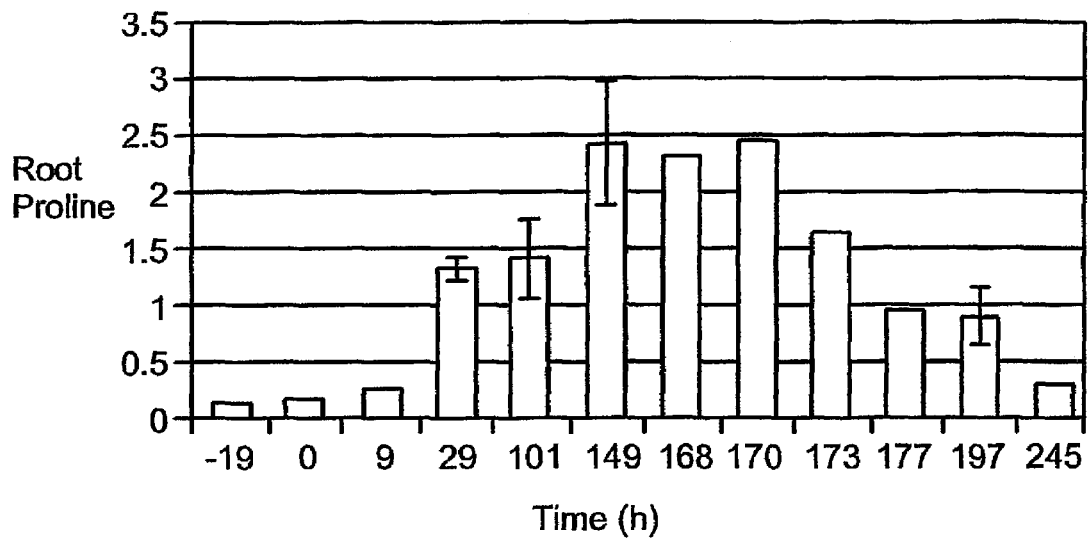
Figure 5C:
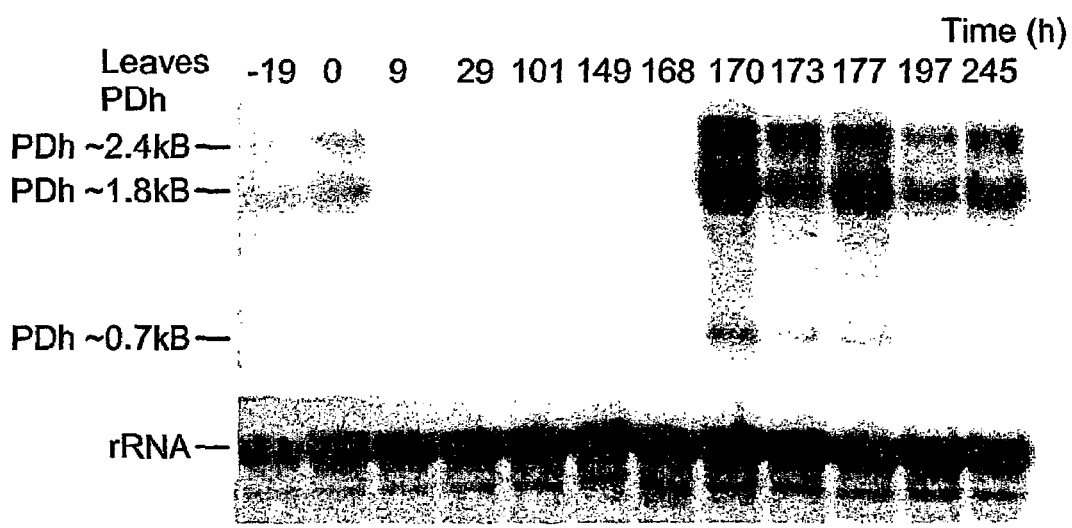

Analysis of PDh expression and free proline level in alfalfa seedlings during salt stress and recovery: Three-week-old alfalfa seedlings were grown in 5 L containers in a liquid medium and exposed to salt stress by replacing the isotonic medium with a medium containing 170 mM NaCl. Samples were taken from roots and leaves and used for the detection of PDh mRNA levels and free proline content estimation (FIGS. 5a-c). Three forms of PDh mRNA were observed, all revealing a similar transcription regulation pattern. PDh mRNA level was strongly reduced, shortly after the imposition of salt stress, and highly increased shortly after salt removal.

Thus, it can be concluded that the changes in proline level are inversely correlated with the changes in PDh mRNA levels. During the seven days of salt stress proline level in roots increased up to twenty-fold compared with the normal level. A gradual decrease in proline level was observed during the three days of recovery from stress.

Example 3

Generation of Transgenic Tobacco Plants Expressing the E. coli proB74 and proA Genes and the Alfala PDh Anti-Sense Fragment, Driven by Constitutive Promoters Two sets of plant vectors were constructed in order to target the GK74 and GPR either to the cytoplasm or to the chloroplasts of the transformed plants.

To target the proteins into the chloroplast, the proB74 and proA coding regions which encode the proline biosynthesis enzyme complex in bacteria were translationally fused downstream to the 5' sequence of pea rbcS, encoding the chloroplast targeting transit peptide of the RUBISCO small subunit. Both genes, with or without the sequence of the transit peptide, were cloned downstream to the CaMV 35S promoter including the TMV omega sequence (FIGS. 6a-g).

Figure 6A:
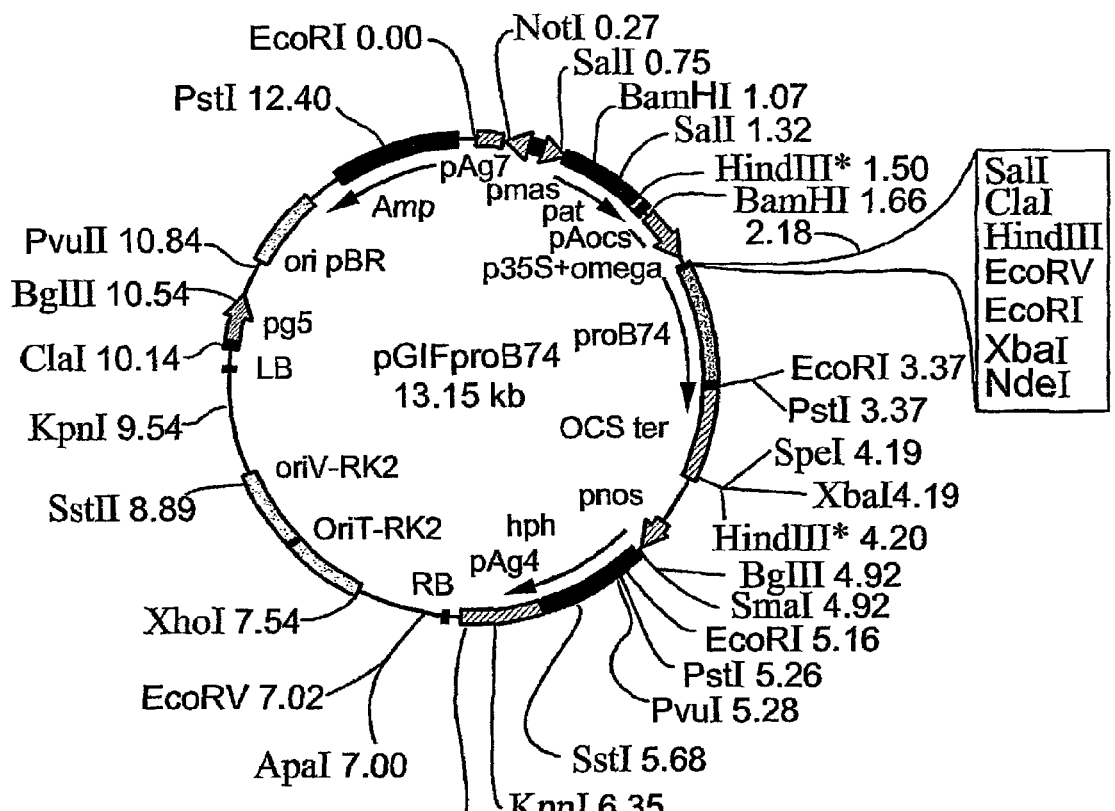
FIGS. 6a-g depict the physical maps of the various plant transformation vectors utilized while reducing the present invention to practice. The transit peptide inclusive, proB74 gene and proA vectors, are shown in FIGS. 6c-d while the same vectors without the transit peptide are shown in FIGS. 6a-b.

The proB74 cassettes with or without the rbcS transit peptide sequence were inserted into the pGIF Agrobacterium-plant shuttle vector (FIGS. 6a, c, f and g). The pGIF vector carries the hph gene linked to the nos promoter as a selectable marker that confers resistance to hygromycin B. It also contains the pat gene driven by the p2 promoter of mannopine synthase from the octopine type T-DNA. This gene confers resistance in planta to the non-selective herbicide BASTA (gluphosinate ammonium).

Figure 6B:
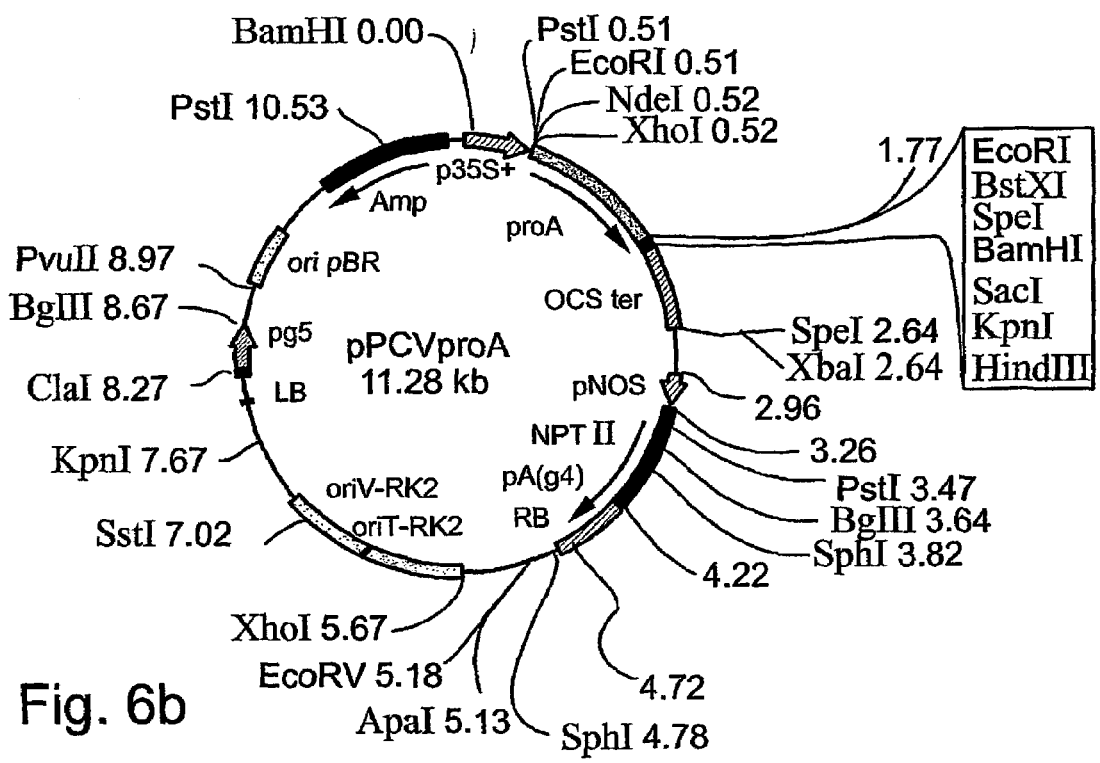

The proA cassettes were inserted into the Agrobacterium-plant shuttle vector pPCV702 (Koncz et al., 1989). This vector carries the nptII gene linked to the nos promoter and confers resistance to kanamycin in plants (FIGS. 6b and d).

Initially, two combinations of plasmids were co-introduced into tobacco (Nicotiana tabacum NN).

The plasmids pPCVproA and pGIFproB74 were used for co-transformation in order to express GK74 and GPR in the cytoplasm of the double transgenic plants. In parallel, the plasmids pPCVproATP and pGIFproB74TP were also used for co-transformation in order to develop double transgenic plants with GK and GPR activity in the chloroplasts. In both cases, Agrobacterium mediated transformations were carried out using a kanamycin and hygromycin B containing medium for selection of double transgenic plants.

Following these transformations, the highly conserved 0.4 Kb PDh fragment (nucleotide coordinates 1110-1494 on Alfalfa PDh cDNA sequence), cloned in anti-sense orientation downstream to the 35S promoter, was introduced along with the proB74-35S promoter construct into transgenic tobacco characterized by a high expression of proA driven by the 35S promoter.

Following this transformation, the following seven types of transgenic tobacco plants were obtained:

(i) 35S promoter-proA, generated by transforming a plant with the vector shown in FIG. 6b.

Figure 6C:
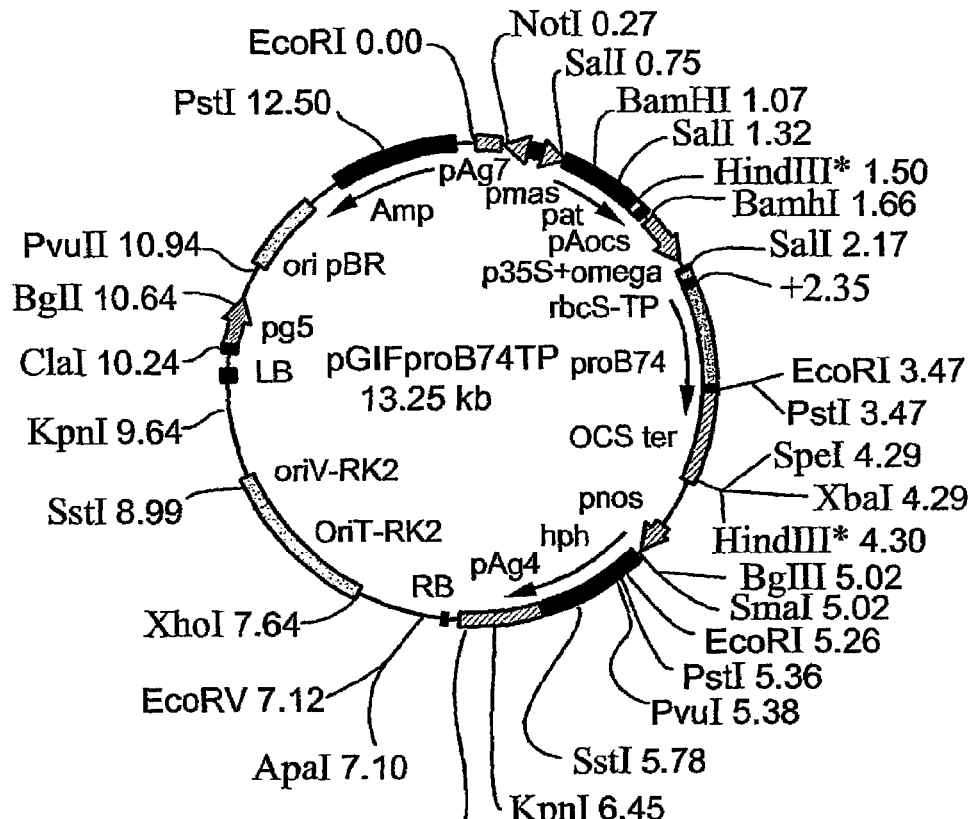
Figure 6D:
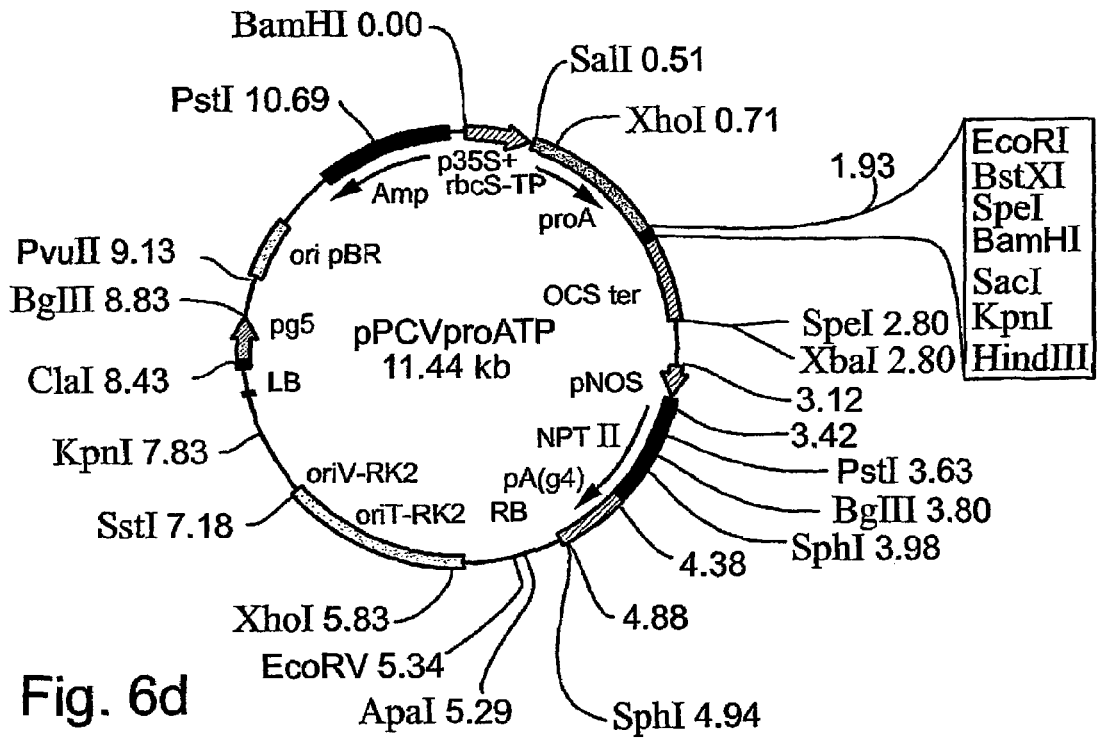

(ii) 35S promoter-rbcS transit peptide sequence-proA, generated by transforming a plant with the vector shown in FIG. 6d.

(iii) 35S promoter-proA and 35S promoter-proB74, generated by co-transforming a plant with the vectors shown in FIGS. 6a-b.

(iv) 35S promoter-rbcS transit peptide sequence-proA and 35S promoter-rbcs transit peptide sequence-proB74, generated by co-transforming a plant with the vectors shown in FIGS. 6c-d.

Figure 6E:
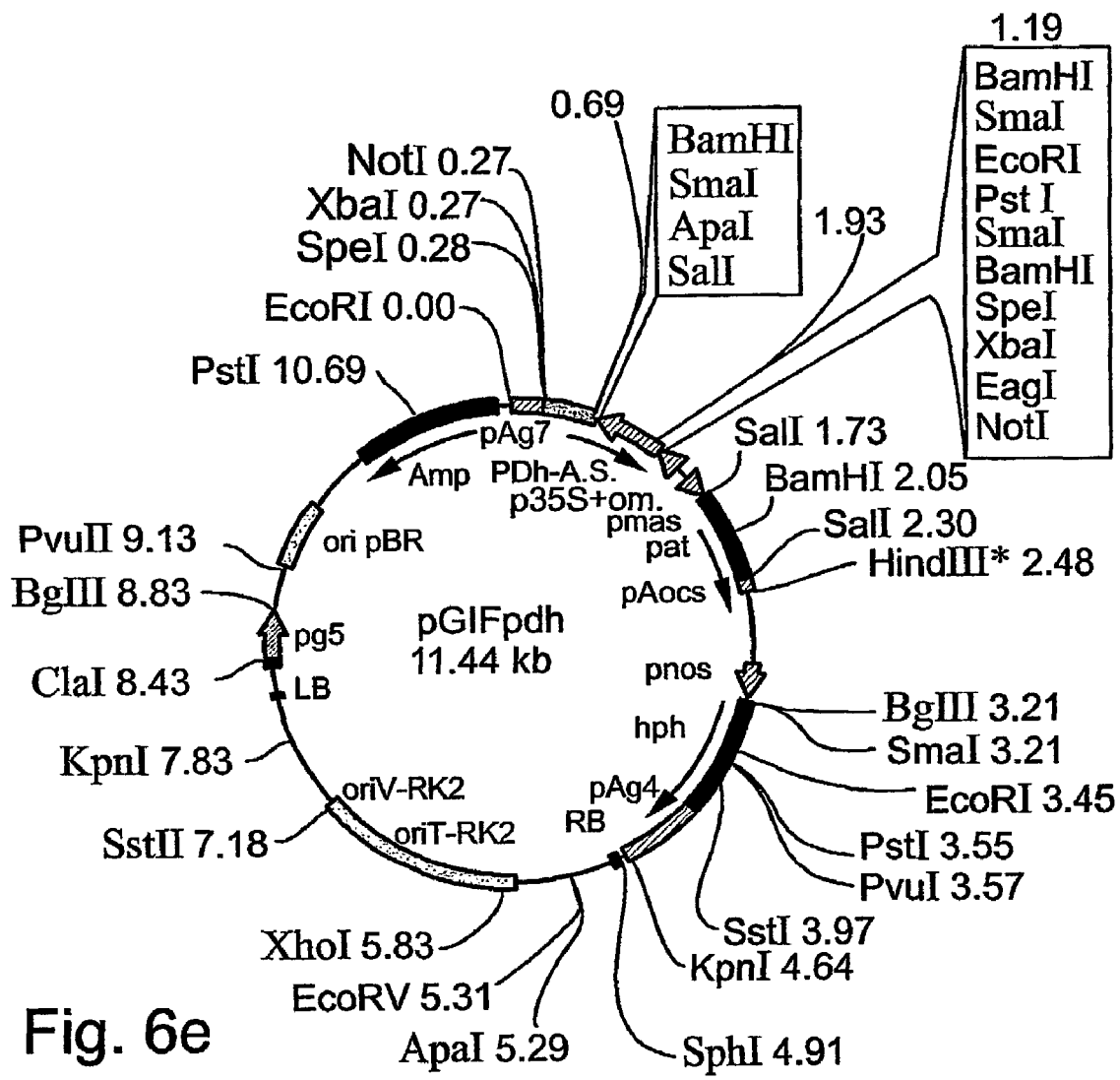
Figure 6F:
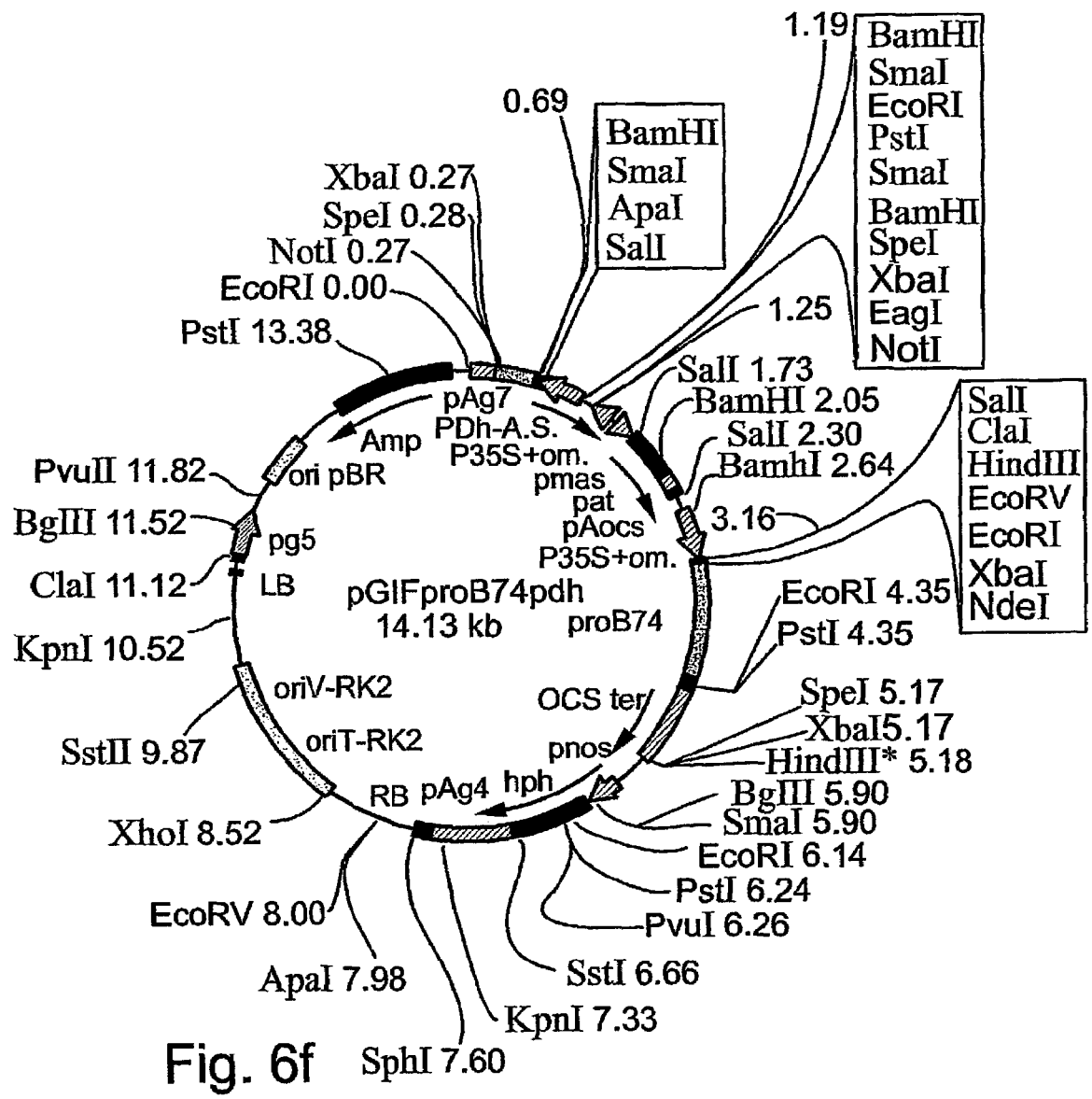

(v) 35S promoter-proA and 35S promoter-proB74 and 35S promoter-PDh anti-sense, generated by transforming the plant described in (i) with the vector shown in FIG. 6f.

Figure 6G:
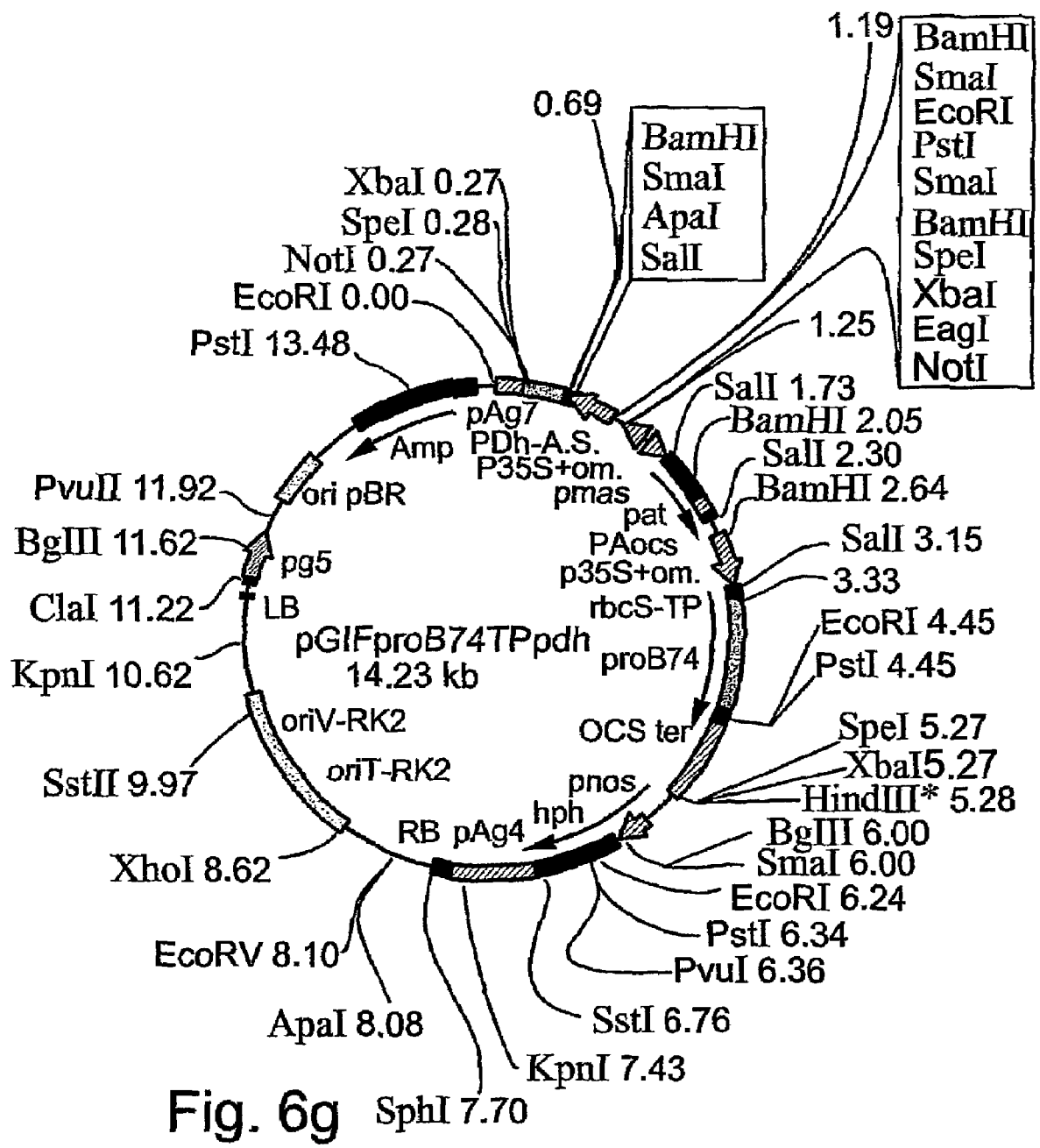

(vi) 35S promoter-rbcS transit peptide sequence-proA and 35S promoter-rbcS transit peptide sequence- proB74 and 35S promoter-PDh anti-sense, generated by transforming the plant described in (ii) with the vector shown in FIG. 6g.

(vii) 35S promoter-PDh cDNA in an antisense orientation, generated by transforming a plant with the vector shown in FIG. 6e.

Figure 7:
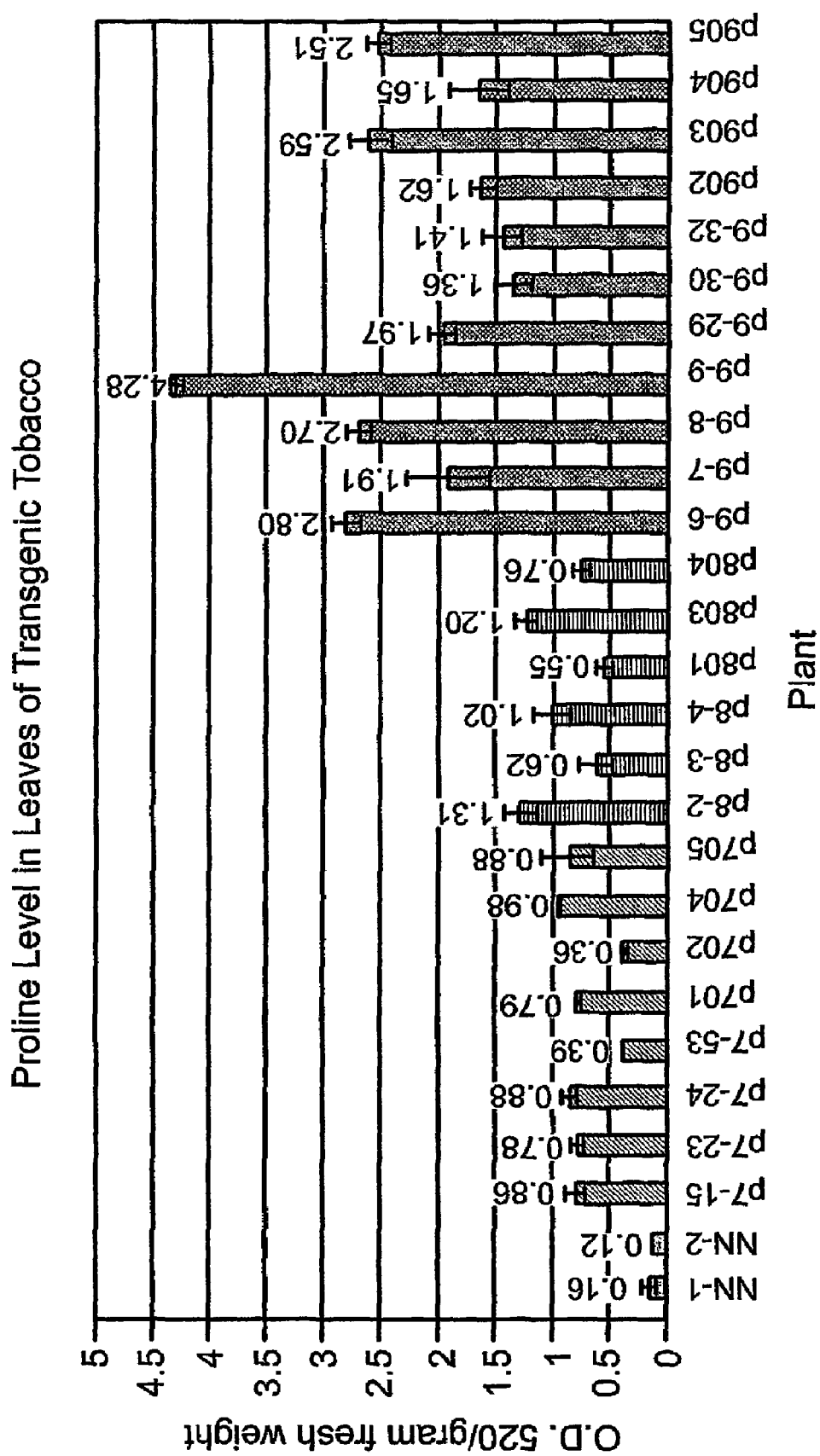
FIG. 7 is a graph depicting an analysis of proline level in leaves of transgenic tobacco plants expressing the PDh anti-sense RNA and the bacterial enzymes GK74 and GPR in the cytosol (p8) or chloroplasts (p9), expressing the PDh anti-sense RNA without the bacterial enzymes (p7), or wild type plants (NN). Plants were grown under saturated irrigation conditions. Proline content was determined as described by Bates et. al. 1973; each point of the data represents the mean value of three replicates.

Increase in proline level in the transgenic tobacco plants expressing the bacterial enzymes GK74 and GPR and the PDh anti-sense RNA: Proline level in transgenic tobacco plants were analyzed by the method of Bates et al., 1973 (FIG. 7). The proline level in plants expressing the antisense construct (p7), in plants expressing the bacterial enzymes in the cytosol (p8) and in plants expressing the bacterial enzymes in the chloroplast (p9) were 8, 10 and 35 fold higher, respectively, then that of the wild type plants.

Figure 8:
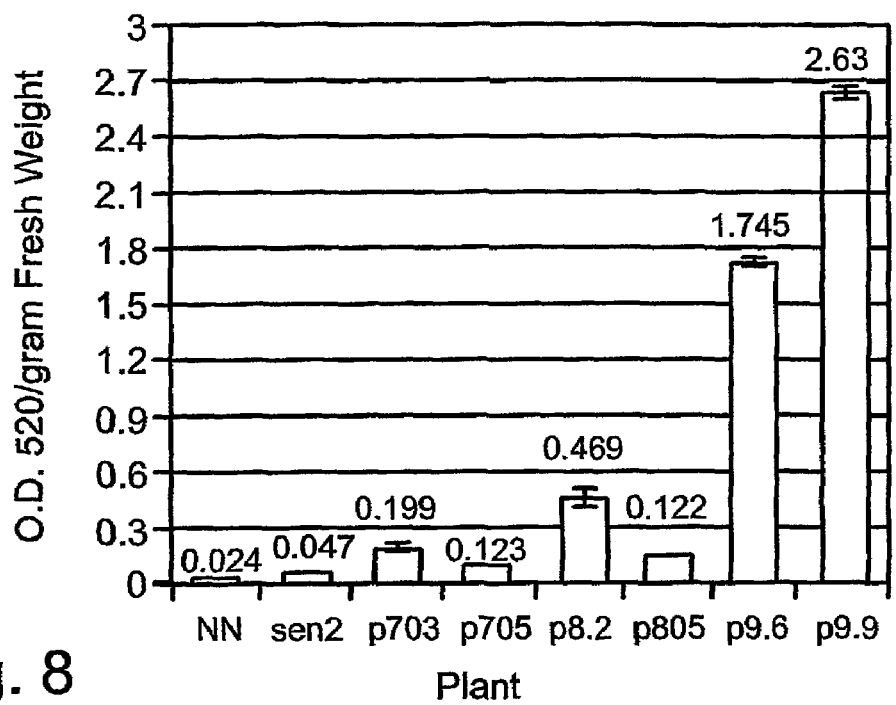
FIG. 8 is a graph depicting an analysis of proline level in leaves of seedlings of an F1 generation resulting from the selfing of the primary tobacco transformants, expressing the PDh anti-sense RNA and the bacterial enzymes GK74 and GPR in the cytosol (p8) or chloroplasts (p9), or expressing the PDh anti-sense RNA without the bacterial enzymes (p7), or wild type plants (NN, sen2). Each measurement was made on a group of about twenty seedlings, grown for ten weeks on solid medium in Petri dishes. Proline level was determined as described by Bates et. al. 1973. Each point of the data represents the mean value of three replicates.

Increase in the proline level in F1 seedlings resulting from selfing primary tobacco transformants expressing the bacterial enzymes GK74 and GPR and the PDh antisense RNA: Proline level in seedlings resultant from the selfing of the p7, p8 and p9 transgenic plants described above, increased up to 8, 19 and 109 times, respectively, in comparison with the wild type plants (FIG. 8). Interestingly, the increase in proline level in the transgenic plants above level of wild type plants is greater in the young seedlings than in the well-developed plants. This indicates that starting from very early stages in the development of genetically modified plants proline is accumulated at high levels, which is useful in order to prepare plants for possible future environmental stress conditions.

Figure 9A:
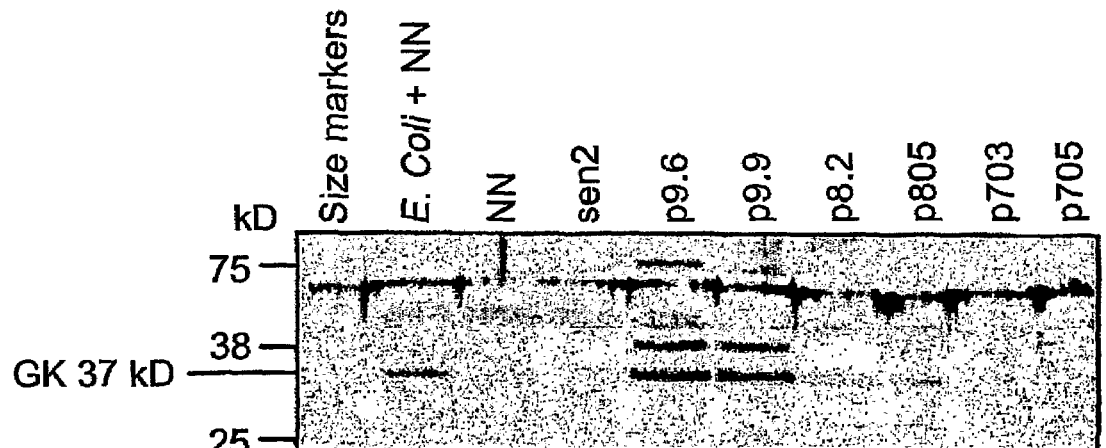
FIGS. 9*a*-*b* are images depicting western blots analysis of either GK74 (FIG. 9*a*) or GPR (FIG. 9*b*) expression in seedlings of an F1 generation resulting from selfing of the primary tobacco transformants expressing the bacterial enzymes in the cytosol (p8) or chloroplasts (p9) along with the PDh anti-sense RNA. P7 plants express only the PDh anti-sense RNA without the bacterial enzymes. NN, Sen2 represents the control plant; lane 1 represents a mixture of total proteins extracted from *E. coli* cells overexpressing GK (about 20 ng) or GPR (about 200 ng) and wild-type plant (about 60 mg).
Figure 9B:
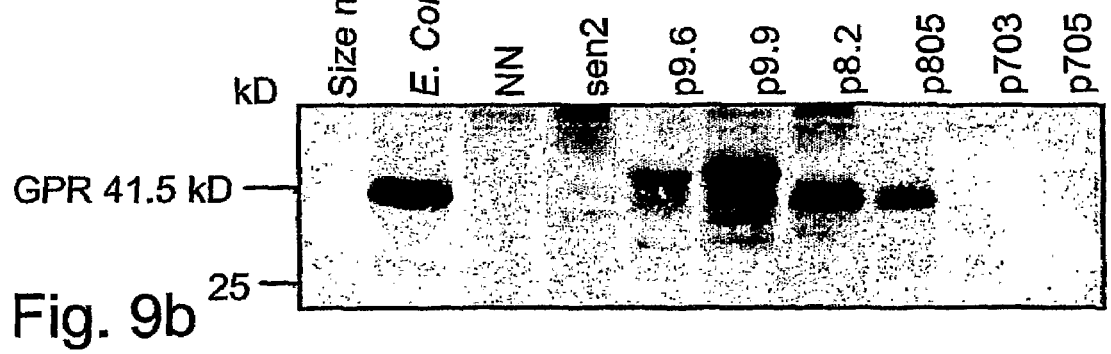

Expression levels of GK74 and GPR in the F1 seedlings: Transgenic tobacco plants resultant from the selling of primary transgenic plants carrying proA and proB74 were subjected to Western blot analysis (FIGS. 9a-b). Plants expressing a relatively high level of glutamyl kinase (GK) and GSA dehydrogenase (GPR) either in the cytosol (p8) or in the chloroplast stroma (p9) were identified. The bacterial enzymes constituted approximately 0.1% of the total protein content of the leaf. In the p9 transgenic plants two forms of GK74 were observed. A 42.5 kD band representing the unprocessed form of GK74, which still possesses the transit peptide and a 37 kD band resulting from the removal of the transit peptide upon uptake into the chloroplast.

Two distinct forms of GPR were also observed. A 47 kD band representing the unprocessed form of GPR still possessing the transit peptide and a 41.5 kD band resulting from the removal of the transit peptide upon entering the chloroplast. Thus, the western analysis revealed that the pre-processed proteins including the SSU leader (RUBISCO small sub-unit leader) are correctly processed when entering the chloroplasts.

Both the GK and GPR bacterial enzymes were found to be highly expressed both in the cytoplasm and chloroplast of plant cells and as such modification of the coding sequence of both bacterial genes to better suit the codon usage of plants is not necessary.

Example 4

Figure 10:
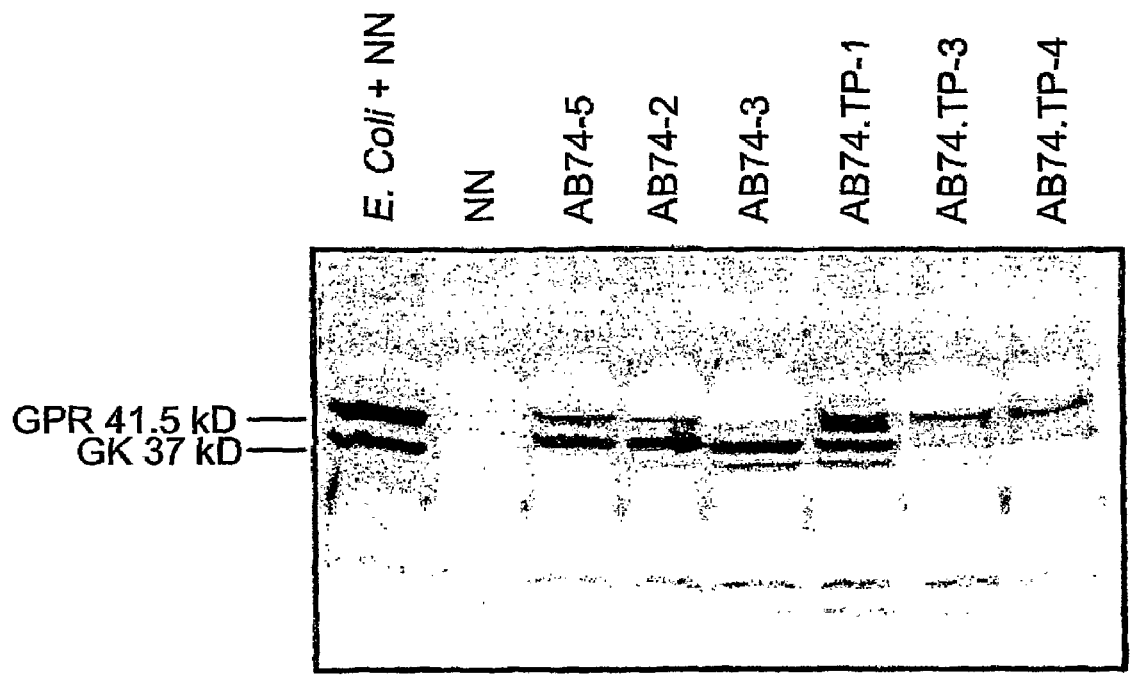
FIG. 10 is an image depicting a western blot analysis of total leaf proteins extracted from control (NN) and transgenic plants. Polyclonal antibodies raised in rabbit against denatured GK or GSD expressed in *E. coli* were used as probes. Lane 1 represents a mixture of total proteins extracted from *E. coli* overexpressing GK and GSD (200 ng) and leaves of a wild-type plant (60 mg).

Expression of GK74 and GPR in the Transgenic Tobacco Plants Expressing the Bacterial Enzymes without the PDh Anti-Sense RNA Following the first round of transformation, transgenic tobacco plants carrying proA and proB74 without the PDh anti-sense cassette were subjected to Western blot analysis (FIG. 10). Plants expressing a relatively high level of glutamyl kinase (GK) and GSA dehydrogenase (GPR) either in the cytosol or in the chloroplast stroma were identified. That analysis showed also that the proteins with the SSU leader (RUBISCO small sub-unit leader) are correctly processed while being taken into the chloroplasts. These results show that both bacterial GK and GPR enzymes are highly expressed either in the cytoplasm or chloroplasts of plants and there is no need to improve the codon usage of both genes in order to obtain a relative high level of expression of bacterial pro genes in plants.

Example 5

Figure 11:
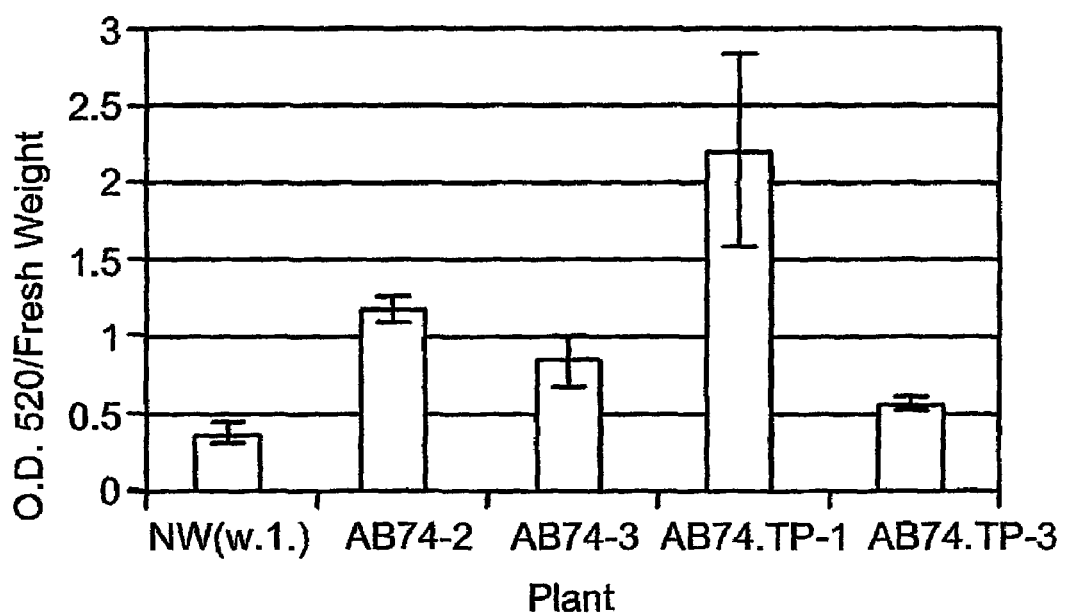
FIG. 11 is a graph depicting the proline level of transgenic tobacco plants grown under normal conditions. Proline content in leaves of the wild-type tobacco (NN) and GK+GSD transgenic lines (AB74 and AB74.TP) was determined as described by Bates et. al. (1973); each point represents the mean value of four replicates.

Increase in Proline Level in the Transgenic Tobacco Plants Expressing the Bacterial Enzymes GK74 and GPR Without the PDh Anti-Sense RNA Proline content was estimated in the transgenic tobacco plants transformed with proA and proB74 and not the PDh anti-sense cassette (FIG. 11). A six-fold increase in proline content, above wild type level, was observed in these plants (AB74TP-1) which express the bacterial GK74 and GPR at high levels.

As is clear from these results, over expression of the biosynthetic enzyme complex can only increase the proline content in plants approximately six times since the activity of proline dehydrogenase and P5C dehydrogenase which comprise the proline catabolic pathway balances the levels of proline. Thus, to enable accumulation of higher levels of proline the activity of these catabolic enzymes must be silenced or downregulated.

Thus, in the present study, transgenic tobacco plants over expressing the *E. coli* proline-insensitive GK74 encoded by proB74, and GPR (also denoted as GSD) encoded by proA, were generated. The exogenous enzymes were targeted either to the cytosol or to the plastids by designing translational fusion with an appropriate transit peptide. Molecular analysis showed that the two prokaryotic enzymes were efficiently expressed in plant cells, correctly targeted to the cytosol or chloroplasts and processed to the mature proteins, which then co-assembled to form active enzymatic complexes in each of the two compartments.

To achieve a concomitant control of proline degradation in the transgenic plants, the full-length gene and cDNA encoding proline dehydrogenase (PDh) were isolated from alfalfa. A PDh DNA segment, corresponding to a highly conserved region among diverse organisms and driven by the CaMV 35S promoter in an anti-sense orientation, was introduced into tobacco and alfalfa, together with proB74 and proA, both driven by the 35S promoter.

Up to 100 fold increase in proline content was observed in the triple transgenic tobacco plants while up to 8 fold increase in proline content was observed in the transgenic plants carrying only the highly conserved PDh antisense segment.

Probing Southern blots containing tobacco, tomato, potato and alfalfa genomic DNA with the alfalfa highly conserved PDh segment, demonstrated cross-hybridization under stringent conditions. The hybridization results show that this alfalfa specific PDh segment can serve as an efficient tool for heterologous anti-sensing of PDh transcription in many plants.

In addition, the promoter region of the alfalfa PDh gene was cloned and sequenced. A unique response of PDh transcription to salt stress and recovery was observed. In alfalfa shoots and roots, PDh mRNA levels are strongly reduced shortly after the imposition of salt stress, and strongly induced shortly after the removal of such a salt stress. These changes in RNA transcript levels reflect the almost immediate response of the PDh promoter to changes in salt content and as such this promoter may serve as an important tool for controlling expression of different genes under stress imposition and recovery.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein, including sequences identified herein by GeneBank Accession Nos., are incorporated by reference in their entirety. Citation or identification of any reference in this application shall not be construed as an admission that such reference is available as prior art to the present invention.

REFERENCES LIST IN ALPHEBETIC ORDER

1. Ballantyne J S, Chamberlin M E 1994 Regulation of cellular amino acid levels. In "Cellular and Molecular Physiology of Cell Volume Regulation" (K Strange ed), CRC Press, Boca Raton, pp. 111-122.
2. Barnett N M, Naylor A W 1966 Amino acid and protein metabolism in Bermuda grass during water stress. Plant Physiol. 41: 1222-1230.
3. Bates L S, Waldren R P, Teare I D 1973 Rapid determination of free proline for water-stress studies. Plant and Soil 39:205-207.
4. Binzel M L, Hasegawa P M, Rhodes D, Handa S, Handa A K, Bressan R A 1987 Solute accumulation in tobacco cells adapted to NaCl. Plant Physiol. 84:1408-1415.
5. Blum A, 1996 Crop responses to drought and the interpretation of adaptation. Plant Growth Regulation. 20:135-148.
6. Blum A, Munns R, Passioura J B, Turner N C 1996 Genetically engineered plants resistant to soil drying and salt stress—how to interpret osmotic relations. Plant Physiol. 110:1051-1051.
7. Boggess S F, Aspinall D, Paleg L G 1976 Stress metabolism. IX. The significance of end-product inhibition of proline biosynthesis and of compartmentation in relation to stress-induced proline accumulation. Aust. J. Plant Physiol. 3: 513-525.
8. Brady C J, Gibson T S, Barlow E W R, Spiers J, Wyn Jones R G 1984 Salt tolerance in plants. I. Ions, compatible solutes and the stability of plant ribosomes. Plant, Cell and Environ. 7: 571-578.
9. Briens M, Larher F 1982 Osmoregulation in halophytic higher plants: a comparative study of soluble carbohydrates, polyols, betaines and free proline. Plant, Cell & Environ. 5: 287-292.
10. Csonka L N 1981 Proline over-production results in enhanced osmotolerance in *Salmonella typhimurium*. Mol. Gen. Genet. 182: 82-86.
11. Csonka L N 1989 Physiological and genetic responses of bacteria to osmotic stress. Microbiol. Reviews 53: 121-147.
12. Csonka L N, Gelvin S B, Goodner B W, Orser C S, Siemieniak D, Slightom J L 1988 Nucleotide sequence of a mutation in the proB gene of *Escherichia coli* that confers proline overproduction and enhanced tolerance to osmotic stress. Gene 64: 199-205.
13. Delauney A J, Verma D P S 1993 Proline biosynthesis and osmoregulation in plants. The Plant Journal 4: 215-223.
14. Dorffling K, Dorifling H, Lesselich G 1993 In vitro-selection and regeneration of hydroxyproline-resistant lines of winter wheat with increased proline content and increased frost tolerance. J. Plant Physiol. 142:222-225.
15. Forlani G, Scainelli D, Nielsen E 1997 Deltal-pyrroline-5-carboxylate dehydrogenase from cultured cells of potato. Plant Physiol. 113: 1413-1418.
16. Fujita T, Maggio A, Garcia-Rios M, Bressan R A, Csonka L N 1998 Comparative analysis of the regulation of expression and structures of two evolutionarily divergent genes for delta1-pyrroline-5-carboxylate synthetase from tomato. Plant Physiol. 118: 661-674.
17. Gibson T S, Spiers J, Brady C J 1984 Salt tolerance in plants. II. In vitro translation of m-RNAs from salt-tolerant and salt-sensitive plants on wheat germ ribosomes: responses to ions and compatible solutes. Plant, Cell & Environ. 7: 579-587.
18. Ginzberg I, Stein H, Kapulnik Y, Szabados L, Strifiov N, Schell J, Koncz C, Zilberstein A 1998 Isolation and characterization of two different cDNAs of DELTA1-pyrroline-5-carboxylate synthase in alfalfa, transcriptionally induced upon salt stress. Plant Molecular Biology 38: 755-764.
19. Hanahan D, 1983 Studies on transformation of *Escherichia coli* with plasmids. J. Mol. Biol. 166: 557-580
20. Handa S, Handa A K, Hasegawa P M, Bressan R A 1986 Proline accumulation and the adaptation of cultured plant cells to water stress. Plant Physiol. 80: 938-945.
21. Hanson A D, Hitz W D 1982 Metabolic responses of mesophytes to plant water deficits. Annu. Rev. Plant Physiol. 33: 163-203.
22. Hare P D, Cress W A 1997 Metabolic implications of stress-induced proline accumulation in plants. Plant Growth Regulation 21: 79-102.
23. Hong-qi Z, Croes A F, Linskens H F 1982 Protein synthesis in germinating pollen of Petunia: role of proline. Planta 154: 199-203.
24. Hu C A, Delauney A J, Verma D P 1992 A bifunctional enzyme (delta1-pyrroline-5-carboxylate synthetase) catalyzes the first two steps in proline biosynthesis in plants. Proc. Natl. Acad. Sci. USA 89: 9354-9358.
25. Jones M M, Osmond C B, Turner N C 1980 Accumulation of solutes in leaves of sorghum and sunflower in response to water deficits. Aust. J. Plant Physiol. 7: 193-205.
26. Katz A, Tal M 1980 Salt tolerance in the wild relatives of cultivated tomato: proline accumulation in callus tissue of *Lycopersicon esculentum* and *L. peruvianum*. Z. Pflanzenphysiol. Bd. 98: 429-435.
27. Ketchum R E B, Warren R C, Klima L J, Lopez-Gutierrez F, Nabors M W 1991 The mechanism and regulation of proline accumulation in suspension cultures of the halophytic grass *Distichlis spicata* L. J. Plant Physiol. 137: 368-374.
28. Kishor P B K, Hong Z, Miao G-H, Hu C-AA, Verma D P S 1995 Overexpression of delta1-pyrroline-5-carboxy- 29. Kiyosue T, Yoshiba Y, Yamaguchi-Shinozaki K, Shinozaki K 1996 A nuclear gene, encoding mitochondrial proline dehydrogenase, an enzyme involved in proline metabolism, is upregulated by proline but downregulated by dehydration in Arabidopsis. The Plant Cell 8: 1323-1335.
30. Koncz C, Martini M, Mayerhofer R, Koncz-Kalman Z, Korber H, Redei G P, Schell J 1989 High-frequency T-DNA-mediated gene tagging in plants. Proc. Natl. Acad. Sci. USA 86:8467-8471.
31. Kueh J S H, Bright S W J 1981 Proline accumulation in a barley mutant resistant to trans-4-hydroxy-L-proline. Planta 153:166-171.
32. Lansac A R, Sullivan C Y, Johnson B E 1996 Accumulation of free proline in sorghum (*Sorghum bicolor*) pollen. Can. J. Bot. 74: 40-45.
33. Leigh R A, Ahmad N, Wyn Jones R G 1981 Assessment of glycinebetaine and proline compartnentation by analysis of isolated beet vacuoles. Planta 153: 34-41.
34. Lone M I, Kueh J S H, Wyn Jones R G, Bright S W J 1987 Influence of proline and glycinebetaine on salt tolerance of cultured barley embryos. J. Exp. Bot. 38: 479-490.
35. Low P S 1985 Molecular basis of the biological compatibility of nature's osmolytes. In "Transport Processes, Iono- and Osmoregulation" (R Gilles, M Gilles-Baillien eds), Springer-Verlag, Berlin, pp. 469-477.
36. Nash D, Paleg L G, Wiskich J T 1982 Effect of proline, betaine and some other solutes on the heat stability of mitochondrial enzymes. Aust. J. Plant Physiol. 9: 47-57.
37. Oaks A, Mitchell D J, Barnard R A, Johnson F J 1970 The regulation of proline biosynthesis in maize roots. Can. J. Bot. 48: 2249-2258.
38. Ober E S, R E 1994 Proline accumulation in maize (*Zea mays* L.) primary roots at low water potentials. I. Requirement for increased levels of abscisic acid. Plant Physiol. 105: 981-987.
39. Paleg L G, Douglas T J, van Daal A, Keech D B 1981 Proline, betaine and other organic solutes protect enzymes against heat inactivation. Aust. J. Plant Physiol. 8: 107-114.
40. Paleg L G, Stewart G R, Bradbeer J W 1984 Proline and glycine betaine influence protein solvation. Plant Physiol. 75: 974-978.
41. Peng Z, Lu Q, Verma D P 1996 Reciprocal regulation of delta1-pyrroline-5-carboxylate synthetase and proline dehydrogenase genes control proline level during and after osmotic stress in plants. Mol. Gen. Genet. 253: 334-341.
42. Pollard A, Wyn Jones R G 1979 Enzyme activities in concentrated solutions of glycinebetaine and other solutes. Planta 144: 291-298.
43. Rhodes D 1987 Metabolic responses to stress. In "The Biochemistry of Plants" (D D Davies ed), Vol. 12, Academic Press, New York, pp. 201-241.
44. Rhodes D, Handa S 1989 Amino acid metabolism in relation to osmotic adjustment in plant cells. In "Environmental Stress in Plants: Biochemical and Physiological Mechanisms", NATO ASI Series, Vol. G19 (J H Cherry ed), Springer, Berlin, pp. 41-62.
45. Rhodes D, Handa S, Bressan R A 1986 Metabolic changes associated with adaptation of plant cells to water stress. Plant Physiol. 82: 890-903.
46. Roosens N H C J, Thu T T, Iskander H M, Jacobs M 1998 Isolation of the ornithine-delta-aminotransferase cDNA and effect of salt stress on its expression in *Arabidopsis thaliana*. Plant Physiol. 117: 263-271.
47. Rudolph A S, Crowe J H, Crowe L M 1986 Effects of three stabilizing agents—proline, betaine and trehalose—on membrane phospholipids. Arch. Biochem. Biophys. 245:134-143.
48. Samaras Y, Bressan R A, Csonka L N, Garcia-Rios M G, Paino D'Urzo M, Rhodes D 1995 Proline accumulation during drought and salinity. In (N Smirnoff ed) "Environment and Plant Metabolism: Flexibility and Acclimation," Bios Scientific Publishers, Oxford, pp 161-187.
49. Sambrook J, Fritsch E F, Maniatis T, 1989 In: Molecular Cloning, Laboratory Manual, second edition, (ed. N. Ford and M. Ferguson). Cold Spring Harbor Laboratory Press, USA
50. Santarius K A 1992 Freezing of isolated thylakoid membranes in complex media. VIII. Differential cryoprotection by sucrose, proline and glycerol. Physiol. Plant. 84: 87-93.
51. Santoro M M, Liu Y, Khan S M A, Hou L-X, Bolen D W 1992 Increased thermal stability of proteins in the presence of naturally occurring osmolytes. Biochemistry 31:5278-5283.
52. Serrano R, Gaxiola R, 1994 Microbial Models and Salt Stress Tolerance in Plants. Critical Rev. in Plant Sci. 13: 121-138.
53. Sharp R E, Wu Y, Voetberg G S, Saab I N, LeNoble M E 1994 Confirmation that abscisic acid accumulation is required for maize primary root elongation at low water potentials. J. Exp. Bot. 45: 1743-1751.
54. Smirnoff N, Stewart G R, 1985 Stress metabolites and their role in coastal plants. Symposium on Coastal Vegetation. 62: 273-278
55. Smirnoff N, Cumbes Q J 1989 Hydroxyl radical scavenging activity of compatible solutes. Phytochem. 28: 1057-1060.
56. Smith L T 1985 Characterization of a gamma-glutamyl kinase from *Escherichia coli* that confers proline overproduction and osmotic tolerance. J. Bacteriol. 164: 1088-1093.
57. Srinivas V, Balasubramanian D 1995 Proline is a protein-compatible hydrotrope. Langmuir 11: 2830-2833.
58. Stewart C R 1981 Proline accumulation: Biochemical aspects. In "Physiology and Biochemistry of Drought Resistance in Plants," (L G Paleg, D Aspinall eds) Academic Press, Sydney, pp 243-259.
59. Stewart G R, Larher F 1980 Accumulation of amino acids and related compounds in relation to environmental stress. In "The Biochemistry of Plants" (B J Miflin ed), Vol. 5, Academic Press, New York, pp. 609-635.
60. Stewart G R, Lee J A 1974 The role of proline accumulation in halophytes. Planta 120: 279-289.
61. Strizhov N, Abraham E, Okresz L, Blickling S, Zilberstein A, Schell J, Koncz C, Szabados L 1997 Differential expression of two P5CS genes controlling proline accumulation during salt-stress requires ABA and is regulated by ABA1, ABI1 and AXR2 in Arabidopsis. Plant J. 12: 557-569.
62. Sumaryati S, Negrutiu I, Jacobs M 1992 Characterization and regeneration of salt- and water-stress mutants from protoplast culture of *Nicotiana plumbaginifolia* (Viviani). Theor. Appl. Genet. 83: 613-619.

63. Szoke A, Miao G H, Hong Z, Verma D P S 1992 Subcellular location of delta1-pyrroline-5-carboxylate reductase in root/nodule and leaf of soybean. Plant Physiol. 99: 1642-1649.
64. Taiz L, Zeiger E 1998 Stress physiology. In ?Plant Physiology, Sinauer Associates, Inc., Publishers, Massachusetts, pp 725-757.
65. Tal M, Katz A 1980 Salt tolerance in the wild relatives of the cultivated tomato: the effect of proline on the growth of callus tissue of *Lycopersicon esculentum* and *L. peruvianum* under salt and water stress. Z. Pflanzenphysiol. Bd. 98: 283-288.
66. Taylor C B 1996 Proline and water deficit: ups and downs. The Plant Cell 8: 1221-1224.
67. Thomas J C, De Armond R L, Bohnert H J 1992 Influence of NaCl on growth, proline, and phosphoenolpyruvate carboxylase levels in *Mesembryanthemum crystallinum* suspension cultures. Plant Physiol. 98: 626-631.
68. Thompson J F 1980 Arginine synthesis, proline synthesis, and related processes. In "The Biochemistry of Plants", Vol 5 (B J Miflin ed) Academic Press, New York, pp. 375-403.
69. Treichel S 1975 The effect of NaCl on the concentration of proline in different halophytes. Z. Pflanzenphysiol. Bd. 76: 56-68.
70. Treichel S 1986 The influence of NaCl on delta1-pyrroline-5-carboxylate reductase in proline-accumulating cell suspension cultures of *Mesembryanthemum nodiflorum* and other halophytes. Plant Physiol. 67: 173-181.
71. Voetberg G S, Sharp R E 1991 Growth of the maize primary root tip at low water potentials. III. Role of increased proline deposition in osmotic adjustment. Plant Physiol. 96: 1125-1130.
72. Yancey P H 1994 Compatible and counteracting solutes. In "Cellular and Molecular Physiology of Cell Volume Regulation" (K Strange ed), CRC Press, Boca Raton, pp. 81-109.
73. Yoshiba Y, Kiyosue T, Nakashima K, Yamaguchi-Shinozaki K, Shinozaki K 1997 Regulation of levels of proline as an osmolyte in plants under water stress. Plant Cell Physiol. 38: 1095-1102.
74. Zhang C S, Lu Q, Verma D P 1995 Removal of feedback inhibition of delta1-pyrroline-5-carboxylate synthetase, a bifunctional enzyme catalyzing the first two steps of proline biosynthesis in plants. J. Biol. Chem. 270: 20491-20496.

What is claimed is:

1. A nucleic acid construct comprising:
(a) a first polynucleotide region encoding a first enzyme selected from the group consisting of gamma-glutamyl kinase (GK), gamma-glutamylphosphate reductase (GPR or GSD), delta-pyrroline-5-carboxylate reductase (P5CR), or delta-pyrroline-5-carboxylate synthase (P5CS) and a first leader peptide being in frame thereto for targeting said first enzyme into a subcellular organelle of a plant cell.

2. The nucleic acid construct of claim 1, wherein said subcellular organelle is a chloroplast.

3. A plant, plant derived tissue or a plant cell comprising the nucleic acid construct of claim 1.

4. A plant tolerant of environmental stress conditions, the plant comprising an exogenous polynucleotide encoding an enzyme selected from the group consisting of gamma-glutamyl kinase (GK), gamma-glutamylphosphate reductase (GPR or GSD), delta-pyrroline-5-carboxylate reductase (P5CR), or delta-pyrroline-5-carboxylate synthase (P5CS), wherein the exogenous polynucleotide is expressed in the plant in a manner so as to allow accumulation of the enzymes within a subcellular organelle of the plant.

5. The plant of claim 4, wherein the enzyme is expressed within the subcellular organelle of the plant.

6. The plant of claim 4, wherein the enzyme is targeted into the subcellular organelle following expression of the exogenous polynucleotide.

7. The plant of claim 4, wherein said exogenous polynucleotide includes a leader sequence for targeting the enzyme expressed therefrom into the subcellular organelle of the plant.

8. The plant of claim 4, wherein the subcellular organelle is a chloroplast.

9. The plant of claim 4, wherein the environmental stress conditions are selected from the group consisting of high salinity, extreme temperature and drought.

* * * * *

UNITED STATES PATENT AND TRADEMARK OFFICE
CERTIFICATE OF CORRECTION

PATENT NO. : 7,385,106 B2  Page 1 of 1
APPLICATION NO. : 10/181409
DATED : June 10, 2008
INVENTOR(S) : Stein et al.

It is certified that error appears in the above-identified patent and that said Letters Patent is hereby corrected as shown below:

Priority Data:
On the title page, insert a section marked:

Item --[63]   Related U.S. Application Data

"US Application No. 09/490,454, filed January 24, 2000"--

Signed and Sealed this

Sixteenth Day of June, 2009

JOHN DOLL
*Acting Director of the United States Patent and Trademark Office*

SEQUENCE LISTING

```
<160> NUMBER OF SEQ ID NOS: 8

<210> SEQ ID NO 1
<211> LENGTH: 24
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: modified_base
<222> LOCATION: (10)..(10)
<223> OTHER INFORMATION: i
<220> FEATURE:
<221> NAME/KEY: modified_base
<222> LOCATION: (13)..(13)
<223> OTHER INFORMATION: i
<220> FEATURE:
<221> NAME/KEY: modified_base
<222> LOCATION: (19)..(19)
<223> OTHER INFORMATION: i

<400> SEQUENCE: 1
gttyaarytn gtnagrggng chta                                          24

<210> SEQ ID NO 2
<211> LENGTH: 24
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: modified_base
<222> LOCATION: (7)..(7)
<223> OTHER INFORMATION: i
<220> FEATURE:
<221> NAME/KEY: modified_base
<222> LOCATION: (10)..(10)
<223> OTHER INFORMATION: i
<220> FEATURE:
<221> NAME/KEY: modified_base
<222> LOCATION: (13)..(13)
<223> OTHER INFORMATION: i
<220> FEATURE:
```

```
<221> NAME/KEY: modified_base
<222> LOCATION: (16)..(16)
<223> OTHER INFORMATION: i
<220> FEATURE:
<221> NAME/KEY: modified_base
<222> LOCATION: (19)..(19)
<223> OTHER INFORMATION: i

<400> SEQUENCE: 2
ctcrtangcn ckncknarna rrta                                           24

<210> SEQ ID NO 3
<211> LENGTH: 171
<212> TYPE: DNA
<213> ORGANISM: Pisum sativum

<400> SEQUENCE: 3
atggcttcta tgatatcctc ttcagctgtg actacagtca gccgtgcttc tacggtgcaa    60
tcggccgcgg tggctccatt cggcggcctc aaatccatga ctggattccc agttaagaag   120
gtcaacactg acattacttc cattacaagc aatggtggaa gagtaaagtg c            171

<210> SEQ ID NO 4
<211> LENGTH: 1850
<212> TYPE: DNA
<213> ORGANISM: Medicago sativa

<400> SEQUENCE: 4
aggtcaagaa gaaaaaaaaa taatcaaagg aaactggttt tttattcatc atatcaaaac    60
atatatcttc gtgtttatat catatagatc atctttgacc ggttgatggc caccagagta   120
atcccaccaa gaattctaag gaaactccga tacaacaccg ccacaaaacc cttccaacct   180
gcccttacct cgcccgctct cgctcctacg tctaatattt tagaccaaaa accgccatca   240
tcgacaacaa ccctcctccc tcccgacgcc gagctcaact tccacgacgt cgaaaaactc   300
ttttcgcacg tcccaactac caaacttctc aaatcaactg ccatcctcca tgctaccgcg   360
gtcgagccaa tggttgacct cggtacatgg atgttgaggt ctgatctcat gcagaccaat   420
aatcctttac gtaacattgc tatggctacc acacgtgcca cttttttcga tcattttgt    480 gccggagaag atgctatcac cgctggaaaa gtattgccg ggttgaatga agccggttta    540
cgtggaatgc tggtttacgg cgttaagat gctcatgata acgctggctg tgatcgcaat    600
ctcaaaggtt ttcttcacac cgttgatgtc agcagatcgc ttcctccatc ttcggtaagc   660
tttgtgattg tgaagattac tgcaatatgt ccaatgagtt tgcttgaaag aatgagtgat   720
ttgctgagat ggcagaagaa agacccttca tttgttttac catggaagca agattcattg   780
ccaattttct ctgagtcaag tcctttgtac catacaagga agagaccaga gccattaaca   840
gcagaagaag agagtgatct tgatcttgct aacaagagat ccttgagct ttgtcagaaa    900 tgtgtgcaag ccaatattcc attattggtt gatgctgaac atacttcagt tcaacctgct   960
attgattact ttacttactc ttctgctatt atgcataaca aaggtgaaaa ccctattgtg  1020
tttggaaccc ttcagactta tttgaaagat gctaaggaga gaatgttgtt ggcatcaaag  1080
gctgctgaga aaatggggat accaatggga tttaagttgg ttagaggtgc ttatatgtct  1140
agtgaaagaa aattggctgc tgatttgggt tatgcttctc caattcataa cactattaag  1200
gatacacata gtgtttcaa tgattgttca aattacatgc ttgagaagat tgctaatggt  1260
cctggtggag ttgttcttgc aactcataac attgaatcag gaaaattggc tgctgcaaaa  1320
gcacatgaat tagggattgg aaaggtgaac cataagatgg aatttgcaca actatatgga  1380
```

-continued

```
atgtctgagg cactatcttt tggtttaagc aatgcagggt ttcaagttag caagtatatg    1440
ccatttggtc ctgtggagac tgttatgcca tacctcttga aagggctga ggagaataga     1500 ggagtgttgg ctgcatcagg ctttgacagg caactgatga ggaaggagtt ggtcaggaga    1560
gtaaaagctt ctgtgcttta aatttgttgg atgagttgat gggatgtaat aatgtaggca    1620
acagggttca ccattctgtg tacaaattag agagaatcct gtaatttgct taaattttgt    1680
gcattcaagt taatgaaatg tgcatttgtc ttaagtgtat tgatccacat ttccacttgt    1740
ttgtacatta atgccattga attgtttaag aaattgttat tcataaagtg tcttatgtgt    1800
ttgaggtgat tccaaaaaaa aaaaaaaaaa aaaaaaaaa aaaaaaaaa                  1850
```

<210> SEQ ID NO 5
<211> LENGTH: 491
<212> TYPE: PRT
<213> ORGANISM: Medicago sativa

<400> SEQUENCE: 5

```
Met Ala Thr Arg Val Ile Pro Pro Arg Ile Leu Arg Lys Leu Arg Tyr
1               5                   10                  15

Asn Thr Ala Thr Lys Pro Phe Gln Pro Ala Leu Thr Ser Pro Ala Leu
            20                  25                  30

Ala Pro Thr Ser Asn Ile Leu Asp Gln Lys Pro Ser Ser Thr Thr
        35                  40                  45

Thr Leu Leu Pro Pro Asp Ala Glu Leu Asn Phe His Asp Val Glu Lys
    50                  55                  60

Leu Phe Ser His Val Pro Thr Thr Lys Leu Leu Lys Ser Thr Ala Ile
65                  70                  75                  80

Leu His Ala Thr Ala Val Glu Pro Met Val Asp Leu Gly Thr Trp Met
                85                  90                  95

Leu Arg Ser Asp Leu Met Gln Thr Asn Asn Pro Leu Arg Asn Ile Ala
            100                 105                 110

Met Ala Thr Thr Arg Ala Thr Phe Phe Asp His Phe Cys Ala Gly Glu
        115                 120                 125

Asp Ala Ile Thr Ala Gly Lys Ser Ile Ala Gly Leu Asn Glu Ala Gly
    130                 135                 140

Leu Arg Gly Met Leu Val Tyr Gly Val Glu Asp Ala His Asp Asn Ala
145                 150                 155                 160

Gly Cys Asp Arg Asn Leu Lys Gly Phe Leu His Thr Val Asp Val Ser
                165                 170                 175

Arg Ser Leu Pro Pro Ser Ser Val Ser Phe Val Ile Val Lys Ile Thr
            180                 185                 190

Ala Ile Cys Pro Met Ser Leu Leu Glu Arg Met Ser Asp Leu Leu Arg
        195                 200                 205

Trp Gln Lys Lys Asp Pro Ser Phe Val Leu Pro Trp Lys Gln Asp Ser
    210                 215                 220

Leu Pro Ile Phe Ser Glu Ser Ser Pro Leu Tyr His Thr Arg Lys Arg
225                 230                 235                 240

Pro Glu Pro Leu Thr Ala Glu Glu Ser Asp Leu Asp Leu Ala Asn
                245                 250                 255

Lys Arg Phe Leu Glu Leu Cys Gln Lys Cys Val Gln Ala Asn Ile Pro
            260                 265                 270

Leu Leu Val Asp Ala Glu His Thr Ser Val Gln Pro Ala Ile Asp Tyr
        275                 280                 285
```

```
Phe Thr Tyr Ser Ser Ala Ile Met His Asn Lys Gly Glu Asn Pro Ile
    290                 295                 300
Val Phe Gly Thr Leu Gln Thr Tyr Leu Lys Asp Ala Lys Glu Arg Met
305                 310                 315                 320
Leu Leu Ala Ser Lys Ala Ala Glu Lys Met Gly Ile Pro Met Gly Phe
                325                 330                 335
Lys Leu Val Arg Gly Ala Tyr Met Ser Ser Glu Arg Lys Leu Ala Ala
                340                 345                 350
Asp Leu Gly Tyr Ala Ser Pro Ile His Asn Thr Ile Lys Asp Thr His
                355                 360                 365
Lys Cys Phe Asn Asp Cys Ser Asn Tyr Met Leu Glu Lys Ile Ala Asn
    370                 375                 380
Gly Pro Gly Gly Val Val Leu Ala Thr His Asn Ile Glu Ser Gly Lys
385                 390                 395                 400
Leu Ala Ala Ala Lys Ala His Glu Leu Gly Ile Gly Lys Val Asn His
                405                 410                 415
Lys Met Glu Phe Ala Gln Leu Tyr Gly Met Ser Glu Ala Leu Ser Phe
                420                 425                 430
Gly Leu Ser Asn Ala Gly Phe Gln Val Ser Lys Tyr Met Pro Phe Gly
                435                 440                 445
Pro Val Glu Thr Val Met Pro Tyr Leu Leu Arg Arg Ala Glu Glu Asn
450                 455                 460
Arg Gly Val Leu Ala Ala Ser Gly Phe Asp Arg Gln Leu Met Arg Lys
465                 470                 475                 480
Glu Leu Val Arg Arg Val Lys Ala Ser Val Leu
                485                 490

<210> SEQ ID NO 6
<211> LENGTH: 2596
<212> TYPE: DNA
<213> ORGANISM: Medicago sativa

<400> SEQUENCE: 6
aggtcaagaa gaaaaaaaaa taatcaaagg aaactggttt tttattcatc atatcaaaac    60
atatatcttc gtgtttatat catatagatc atctttgacc ggttgatggc caccagagta   120
atcccaccaa gaattctaag gaaactccga tacaacaccg ccacaaaacc cttccaacct   180
gcccttacct cgcccgctct cgctcctacg tctaatattt tagaccaaaa accgccatca   240
tcgacaacaa ccctcctccc tcccgacgcc gagctcaact ccacgacgt cgaaaaactc    300
ttttcgcacg tcccaactac caaacttctc aaatcaactg ccatcctcca tgctaccgcg   360
gtcgagccaa tggttgacct cggtacatgg atgttgaggt ctgatctcat gcagaccaat   420
aatcctttac gtaacattgc tatggctacc acacgtgcca cttttttcga tcattttgt    480
gccggagaag atgctatcac cgctggaaaa gtattgccg ggttgaatga agccggttta    540
cgtggaatgc tggtttacgg cgttgaagat gctcatgata acgctggctg tgatcgcaat   600
ctcaaaggtt ttcttcacac cgttgatgtc agcagatcgc ttcctccatc ttcggtaatc   660
tcttctttat ttcatctctt tatttcaaaa tgtaactgtt tcttttttt gctttttgg    720
ttcggtttct tcattgtcac agaagagaga tgcaatctgc tttaatggat ccaaattcaa   780
ttgagaataa ccgttttcac ggtgccgagt tcggcattcg tgactgcaac cgcaatttaa   840
tacagcacta ctgatgacgt tgttgctgct gatgtgatgt gacgtgacgt atctggtgtc   900
cgtgtctgtg tctgattcaa tggctcaagg agggaatgga aagaaaact aagcatggaa    960
```

-continued

```
caatggaaat tggaatttga ttcatgaaaa tcaatcaaag catgattgg aacaatggaa    1020 atgggaatgg gaattggaac aaacaaacaa ttgttttgg taaaagattc tcaagcacta    1080
ataagccaca cagaaaaaaa aactgtggtt gctggtgcat ttttaatact tttttttaaaa   1140 ttatgtaaaa aaaattaggt tatgaatttg agtggttgtt ttaattttaa gtttaatatt    1200
atcattatga atgttatgta ctaatgtttt caaatttaaa cttttttctg tgtataggta    1260
agctttgtga ttgtgaagat tactgcaata tgtccaatga gtttgcttga aagaatgagt    1320
gatttgctga gatggcagaa gaaagacct tcatttgttt taccatggaa gcaagattca    1380
ttgccaattt tctctgagtc aagtcctttg taccatacaa ggaagagacc agagccatta   1440
acagcagaag aagagagtga tcttgatctt gctaacaaga gattccttga gctttgtcag    1500
aaatgtgtgc aagccaatat tccattattg gttgatgctg aacatacttc agttcaacct    1560
gctattgatt actttactta ctcttctgct attatgcata caaaggtga aaaccctatt     1620 gtgtttggaa cccttcagac ttatttgaaa gatgctaagg agagaatgtt gttggcatca    1680
aaggctgctg agaaaatggg gataccaatg ggatttaagt tggttagagg tgcttatatg    1740
tctagtgaaa gaaaattggc tgctgatttg gttatgctt ctccaattca taacactatt     1800
aaggatacac ataagtgttt caatgattgt tcaaattaca tgcttgagaa gattgctaat    1860
ggtcctggtg gagttgttct tgcaactcat aacattgaat caggtatata ttatatgata    1920
ttatgataat gatttatatt aatgtatgca attgaggggt atgagtttga tttaattaat    1980 gattttgta taggaaaatt ggctgctgca aaagcacatg aattagggat tggaaaggtg     2040
aaccataaga tggaatttgc acaactatat ggaatgtctg aggcactatc ttttggttta   2100
agcaatgcag ggtttcaagt tagcaagtat atgccatttg gtcctgtgga gactgttatg    2160
ccatacctct tgagaagggc tgaggagaat agaggagtgt tggctgcatc aggctttgac   2220
aggcaactga tgaggtaaaa atttcaaaaa aatttaccat ttcatattta ctcgttaatt    2280
ttgtgtgatt ctgtttctga cattgaattt gttttgtgta acaggaagga gttggtcagg   2340
agagtaaaag cttctgtgct ttaaatttgt tggatgagtt gatgggatgt aataatgtag    2400
gcaacagggt tcaccattct gtgtacaaat tagagagaat cctgtaattt gcttaaattt   2460
tgtgcattca agttaatgaa atgtgcattt gtcttaagtg tattgatcca catttccact   2520
tgtttgtaca ttaatgccat tgaattgttt aagaaattgt tattcataaa gtgtcttatg   2580
tgtttgaggt gattcc                                                    2596
```

<210> SEQ ID NO 7
<211> LENGTH: 722
<212> TYPE: DNA
<213> ORGANISM: Medicago sativa

<400> SEQUENCE: 7

```
taaatgccac catgaaactt acacacaatt atgagatttt agataaagat gtcaaacttg     60
acagtatttg aattgttaac aaattttgt taatgttgtt ttttaacag tgtctataat      120 tagaaaaatg aagaaatagg aaggtactag agactagaga gtaaacaatt tcatcatact     180
ttatgtagga agtaataaat attagtcaaa ggaaggaaga gataaaaaga atctatcaac     240
atgagtctag tgagtaagtt ccaacacatg atgagtgtaa tcctcgtgga gtctgtgtca    300
gcattttgca cgtacttcgt acaaatctta aattttggaa ctatcaattt cttagctgtg    360
tttgttttgt ttggtgcaac aacttaccac ttgtacctct tagctgccat ccatttcaac    420
accattccat ttactcatat taaaccaact tactccaata atttaggaaa catgaccaaa    480
```

-continued

```
acaatttttt aaattaaacc aacttactca tattggtcag aaccaaaaca aacttaacaa      540
acttactcct atccaccaac caattcacac atcatccact tgacttcttc tttaactttt      600
ttaatcacac cctcctttct tttagcatcc acattcttct tttcacctct atttatacat      660
taccttctaa ttcattctca cttcacaagc atacatattt tgtatctca ttacattttc       720 at                                                                     722
```

<210> SEQ ID NO 8
<211> LENGTH: 1439
<212> TYPE: DNA
<213> ORGANISM: Medicago sativa

<400> SEQUENCE: 8

```
ccatggaaac caccacgaaa caacacaacc aaaaatccat caaaaccata acagatcata      60
tgcagacaca aatcacaact ttcgtgaccg accaatcacc acctacgttg cgagcaaaca     120
aaacctccat ccaccgttaa gagagaaaac agatctggta tcaaccacca cataccaaaa     180
agactaactc aagccatcaa cgttgaacag tcagagaaac agaatcgtaa cacaattcat     240
gactccataa gagatcgacc gtcagaacca ccgccaaaac cgccgtaaag gaccatcggc     300
agatctggag gtaggtgggc ggagggctca agcctcttgt cgcaccacca taaacatcct     360
ctacatctta agaagatata ttggattttt gggcggcgac aacaagtttt gtgttgagag     420
aaggcaggga aaagagaagc tagggttttt acgtgtcttt caacaactct ttaattaata     480
ctatatacgc tacttccaaa gtattatttt ttctttaatg aaaaacaaag aaatagttga     540
ttaagataat ttgataaaat aacatctttt ctcttttaat taatacattt tttaatatgt     600
ggggtaaaaa tcttaaacgc attcttttg aacatagggg gtagtaattt taaagagtta      660
tgaacatttt tttaaacgaa ttggttaata cccatttgaa acttcccccc atttatgaga     720
ttttacaaaa ggtttcaaac ttgcaaatat ttgaattgtt aacaatttt tgttaattgt      780 tttttttta atagtgtcta ttattaggaa aatgaagaaa taggaagcta ctagagagtc      840
cttcaaaaaa ggaaggtact agagagtaaa caatttcatc atactttatg taggaagtaa     900
taaatactta gtcaaaggaa gagatgaaaa gaatctataa acatgactac atgagttatg     960
gtgtttatag tgagtaagtt ccaacacatg atgagtgtat ccgcgtagag tctgtgtcag    1020
cattttgctc gtacttcgta caaatcttaa attttggaac catcaatttc ttagctgtgt    1080
ttgttttgtt tgttgcaaca acttaccact tgtacctctt agctgccatc cattttaca    1140 acatcattta ctcatattaa accaacttac tccataatt taggaaacat gactaaaaca     1200 atttttctaaa ttaaacaaac ttactcatat tggtcagaac caaaacaaac ttaacaaact    1260
tactcctatc caccaaccaa ttcacacatc atccacttga cttcttcttt aactttttta    1320
atcacaccct cctttctttt agcatccaca ttcttctttt cacctctatt tatacattac    1380
cttctaattc attctcactt cacaagcata cacattttg tatctcatta cattttcat      1439
```